US007858590B2

(12) United States Patent
Lowenstein et al.

(10) Patent No.: US 7,858,590 B2
(45) Date of Patent: Dec. 28, 2010

(54) TREATMENT OF PARKINSON'S DISEASE AND RELATED DISORDERS

(75) Inventors: Pedro Lowenstein, Los Angeles, CA (US); Maria Castro, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 426 days.

(21) Appl. No.: 11/572,397

(22) PCT Filed: Aug. 11, 2005

(86) PCT No.: PCT/US2005/029192

§ 371 (c)(1), (2), (4) Date: Jan. 4, 2008

(87) PCT Pub. No.: WO2006/020996

PCT Pub. Date: Feb. 23, 2006

(65) Prior Publication Data

US 2008/0167216 A1 Jul. 10, 2008

Related U.S. Application Data

(60) Provisional application No. 60/600,629, filed on Aug. 11, 2004.

(51) Int. Cl.
*C12N 15/11* (2006.01)
(52) U.S. Cl. .................................................. 514/44 A
(58) Field of Classification Search .................... 514/44
See application file for complete search history.

(56) References Cited

U.S. PATENT DOCUMENTS

| | | |
|---|---|---|
| 5,139,941 A | 8/1992 | Muzyczka et al. |
| 5,173,414 A | 12/1992 | Lebkowski et al. |
| 5,399,346 A | 3/1995 | Anderson et al. |
| 5,844,079 A | 12/1998 | Ingham et al. |
| 6,165,747 A | 12/2000 | Ingham et al. |
| 6,271,363 B1 | 8/2001 | Ingham et al. |
| 6,384,192 B1 | 5/2002 | Ingham et al. |
| 6,576,237 B1 | 6/2003 | Ingham et al. |
| 6,607,913 B1 | 8/2003 | Ingham et al. |
| 6,630,148 B1 | 10/2003 | Ingham et al. |
| 7,135,454 B2 | 11/2006 | Chimienti et al. |
| 7,138,492 B2 | 11/2006 | Miao et al. |
| 2003/0054437 A1 | 3/2003 | Ingham et al. |
| 2003/0104995 A1 | 6/2003 | Reilly |
| 2003/0162698 A1 | 8/2003 | Galdes et al. |
| 2003/0186357 A1 | 10/2003 | Ingham et al. |
| 2004/0072345 A1 | 4/2004 | Altaba et al. |
| 2004/0092010 A1 | 5/2004 | Altaba et al. |

FOREIGN PATENT DOCUMENTS

| | | |
|---|---|---|
| WO | WO92/01070 | 1/1992 |
| WO | WO93/03769 | 3/1993 |
| WO | WO97/00117 | 1/1997 |
| WO | WO99/04775 | 2/1999 |
| WO | WO03/070265 | 8/2003 |

OTHER PUBLICATIONS

Akazawa et al., The Upregulated Expression of Sonic Hedgehog in Motor Neurons After Rat Facial Nerve Axotomy, The Journal of Neuroscience, (Sep. 8, 2004), pp. 7923-7930, 24(36).
Alzghoul et al., Ectopic Expression of IGF-I and Shh by Skeletal Muscle Inhibits Disuse-Mediated Skeletal Muscle Atrophy and Bone Osteopenia In Vivo, The FASEB Journal, (Jan. 2004), pp. 221-223, 18(1).
Bergstein et al., In Vivo Enhanced Expression of Patched Dampens the Sonic Hedgehog Pathway, Molecular Therapy, (Aug. 2002), pp. 258-264, 6(2).
Bezard et al., Sonic Hedgehog Is a Neuromodulator in the Adult Subthalamic Nucleus, The FASEB Journal, (Dec. 2003), pp. 2337-2338, 17(15).
Bhardwaj et al., Sonic Hedgehog Induces The Proliferation of Primitive Human Hematopoietic Cells Via BMP Regulation, Nature Immunology, (Feb. 2001), pp. 172-180, 2(2).
Bilang-Bleuel et al., Intrastriatal Injection of an Adenoviral Vector Expressing Glial-Cell-Line-Derived Neurotrophic Factor Prevents Dopaminergic Neuron Degeneration and Behavioral Impairment in a Rat Model of Parkinson Disease, Proceedings of the National Academy of Sciences, USA, (Aug. 1997), pp. 8818-8823, 94.
Bjorklund et al., Towards a Neuroprotective Gene Therapy for Parkinson's Disease: Use of Adenovirus, AAV and Lentivirus Vectors For Gene Transfer of GDNF to the Nigrostriatal System in the Rat Parkinson Model, Brain Research, (Dec. 15, 2000), pp. 82-98, 886(1-2).
Bohn, M.C., A Commentary on Glial Cell Line-Derived Neurotrophic Factor (GDNF). From a Glial Secreted Molecule to Gene Therapy, Biochemical Pharmacology, (Jan. 15, 1999), pp. 135-142, 57(2).
Cass, W.A., GDNF Selectively Protects Dopamine Neurons Over Serotonin Neurons Against the Neurotoxic Effects of Methamphetamine, the Journal of Neuroscience, (Dec. 15, 1996), pp. 8132-8139, 16(24).
Castro et al., Gene Therapy for Parkinson's Disease: Recent Achievements and Remaining Challenges, Histology and Histopathology, (2001), pp. 1225-1238, 16.

(Continued)

*Primary Examiner*—J. E Angell
(74) *Attorney, Agent, or Firm*—Seth D. Levy; Davis Wright Tremaine LLP

(57) ABSTRACT

Described herein are compositions and methods for the treatment of Parkinson's disease (PD) and/or to protect dopaminergic nigrostriatal neuronal cell bodies from 6-OHDA-induced neurotoxicity in a mammal. In various embodiments of the invention, the dopaminergic neuron differentiation factor sonic hedgehog (Shh) and/or its downstream transcription factor target Gli-1 are used in connection with gene therapeutic techniques or direct peptide injection for the aforementioned indications. Kits useful in practicing the inventive method are also disclosed, as are animal models useful for studying various neurodegenerative conditions.

12 Claims, 9 Drawing Sheets

OTHER PUBLICATIONS

Choi-Lundberg et al., Dopaminergic Neurons Protected From Degeneration by GDNF Gene Therapy, Science, (Feb. 7, 1997), 275.

Connor et al., Differential Effects of Glial Cell Line-Derived Neurotrophic Factor (GDNF) in the Striatum and Substantia Nigra of the Aged Parkinsonian Rat, (1999), pp. 1936-1951, 6.

Connor et al., Glial Cell Line-Derived Neurotrophic Factor (GDNF) Gene Delivery Protects Dopaminergic Terminals From Degeneration, Experimental Neurology, (May 2001), pp. 83-95, 169(1).

Dass et al., Behavioural and Immunohistochemical Changes Following Supranigral Administration of Sonic Hedgehog in 1-Methyl-4-Phenyl-1,2,3,6-Tetrahydropyridine-Treated Common Marmosets, Neuroscience, (2002), pp. 99-109, 114(1).

Eberhardt et al., Protection by Synergistic Effects of Adenovirus-Mediated X-Chromosome-Linked Inhibitor of Apoptosis and Glial Cell Line-Derived Neurotrophic Factor Gene Transfer in the 1-Methyl-4-Phenyl-1,2,3,6-Tetrahydropyridine Model of Parkinson's Disease, The Journal of Neuroscience, (Dec. 15, 2000), pp. 9123-9134, 20(24).

Edwards et al., Sonic Hedgehog Gene-Enhanced Tissue Engineering for Bone Regeneration, Gene Therapy, (Jan. 2005), pp. 75-86, 12(1).

Gill et al., Direct Brain Infusion of Glial Cell Line-Derived Neurotrophic Factor in Parkinson Disease, Nature Medicine, (May 2003), pp. 589-595, 9(5).

Grande et al., Stem Cells As Platforms for Delivery of Genes to Enhance Cartilage Repair, The Journal of Bone and Joint Surgery American, (2003), pp. 111-116, 85 (A Suppl).

Hurtado-Lorenzo et al., Adenovirus-Mediated Gene Transfer of Shh, GLI-1 and Nurr1 in a Rat Model of Parkinson's Disease, Society of Neuroscience Abstracts, (2000), Abstract No. 666.17.

Hurtado-Lorenzo et al., Differentiation and Transcription Factor Gene Therapy in Experimental Parkinson's Disease: Sonic Hedgehog and Gli-1, But Not Nurr-1, Protect Nigrostriatal Cell Bodies From 6-OHDA-Induced Neurodegeneration, Molecular Therapy, (Sep. 2004), pp. 507-524, 10(3).

Kirik et al., Long-Term rAAvV-Mediated Gene Transfer of GDNF in the Rat Parkinson's Model: Intrastriatal But Not Intranigral Transduction Promotes Functional Regeneration in the Lesioned Nigrostriatal System, the JournalOf Neuroscience, (Jun. 15, 2000), pp. 4686-4700, 20(12).

Kordower et al., Clinicopathological Finding Following Intraventricular Glial-Derived Neurotrophic Factor Treatment in a Patient With Parkinson's Disease, Annals of Neurology, (Sep. 1999), pp. 419-424, 46(3).

Kordower et al., Neurodegeneration Prevented by Lentiviral Vector Delivery of GDNF in Primate Models of Parkinson's Disease, Science, (Oct. 27, 2000), pp. 767-773, 290.

Kubo et al., Hedgehog Signaling Pathway is a New Therapeutic Target for Patients With Breast Cancer, Cancer Research, (Sep. 1, 2004), pp. 6071-6074, 64.

Kusano et al., Sonic Hedgehog Induces Arteriogenesis in Diabetic Vasa Nervorum and Restores Function in Diabetic Neuropathy, Arteriosclerosis Thrombosisand Vascular Biology, (2004), pp. 2102-2107, 24.

Lowenstein et al., Neuronal-Specific Expression of Gli-1 is Neuroprotective in Experimental Parkinson's Disease, Without an Increase in Efficacy When Compared to a Pancellular Promoter, Society for Neuroscience Abstracts, (2003), Abstract No. 451.1.

Miao et al., Sonic Hedgehog Promotes the Survival of Specific CNS Neuron Populations and Protects These Cells From Toxic Insult In Vitro, The Journal of Neuroscience, (Aug. 1, 1997), pp. 5891-5899, 17(15).

Nutt et al., Randomized, Double-Blind Trial of Glial Cell Line-Derived Neurotrophic Factor (GDNF) in PD, Neurology, (Jan. 14, 2003), pp. 69-73, 60(1).

Pola et al., Postnatal Recapitulation of Embryonic Hedgehog Pathway in Response to Skeletal Muscle Ischemia, Circulation, (2003), pp. 479-485, 108.

Suwelack et al., Neuronal Expression of the Transcription Factor Gli1 Using the T$\alpha$1 $\alpha$-Tublin Promoter Is Neuroprotective in an Experimental Model of Parkinson's Disease, Gene Therapy, (2004), pp. 1742-1752, 11.

Rostral →

→ Caudal

TREATMENT OF PARKINSON'S DISEASE AND RELATED DISORDERS

This application is the National Phase of International Application PCT/US05/29192, filed Aug. 11, 2005, which designated the U.S. and that International Application was published under PCT Article 21(2) in English. This application also includes a claim of priority under 35 U.S.C. §119(e) to U.S. provisional patent application No. 60/600,629, filed Aug. 11, 2004.

FIELD OF THE INVENTION

The invention relates to the field of neurodegenerative disorders, and, in particular embodiments, to Parkinson's disease.

BACKGROUND OF THE INVENTION

Treatments for Parkinson's disease (PD), although effective, do not halt the progressive loss of substantia nigra dopaminergic neurons. Eventually, clinical symptoms become resistant to treatments relying on the integrity of nigrostriatal neurons, such as L-DOPA [S. Mandel et al., *Neuroprotective strategies in Parkinson's disease: an update on progress, CNS Drugs*, 17:729-762 (2003)]. Preserving viable nigrostriatal neurons would delay disease progression and thus prolong treatments' efficacy [J. H. Kordower et al., *Neurodegeneration prevented by lentiviral vector delivery of GDNF in primate models of Parkinson's disease, Science*, 290:767-773 (2000); D. Kirik et al., *Long-term rAAV-mediated gene transfer of GDNF in the rat Parkinson's model: intrastriatal but not intranigral transduction promotes functional regeneration in the lesioned nigrostriatal system, J. Neurosci.*, 20:4686-4700 (2000); D. L. Choi-Lundberg et al., *Dopaminergic neurons protected from degeneration by GDNF gene therapy, Science*, 275:838-841 (1997); M. G. Castro et al., *Gene therapy for Parkinson's disease: recent achievements and remaining challenges, Histol. Histopathol.*, 16:1225-1238 (2001)]. Glial-cell-derived neurotrophic factor (GDNF) protects nigral dopaminergic cell bodies and their striatal axon terminals from in vitro and in vivo neurotoxicity induced by 6-hydroxydopamine (6-OHDA) [D. L. Choi-Lundberg et al., *Dopaminergic neurons protected from degeneration by GDNF gene therapy, Science*, 275:838-841 (1997)4], MPTP [J. H. Kordower et al., *Neurodegeneration prevented by lentiviral vector delivery of GDNF in primate models of Parkinson's disease, Science*, 290:767-773 (2000)], or methamphetamine [W. A. Cass, *GDNF selectively protects dopamine neurons over serotonin neurons against the neurotoxic effects of methamphetamine, J. Neurosci.*, 16:8132-8139 (1996)], and possibly also in PD patients [S. S. Gill et al., *Direct brain infusion of glial cell line-derived neurotrophic factor in Parkinson disease, Nat. Med.*, 9:589-595 (2003)].

GDNF has been delivered into the brain using adenovirus (RAd)-, adeno-associated virus-, herpes simplex virus type 1 (HSV-1)-, or lentiviral-derived vectors or by direct peptide injection [M. G. Castro et al., *Gene therapy for Parkinson's disease: recent achievements and remaining challenges, Histol. Histopathol.*, 16:1225-1238 (2001); S. S. Gill et al., *Direct brain infusion of glial cell line-derived neurotrophic factor in Parkinson disease, Nat. Med.*, 9:589-595 (2003); A. Bjorklund et al., *Towards a neuroprotective gene therapy for Parkinson's disease: use of adenovirus, AAV and lentivirus vectors for gene transfer of GDNF to the nigrostriatal system in the rat Parkinson model, Brain Res.*, 886:82-98 (2000); E. A. Burton et al., *Gene therapy progress and prospects: Parkinson's disease, Gene Ther.*, 10: 1721-1727 (2003)]. Despite its neuroprotective actions, GDNF can have untoward effects (i.e., reduction of tyrosine hydroxylase mRNA in nigrostriatal neurons, aberrant morphologies of striatal tyrosine hydroxylase-immunoreactive axons, and increased cell death following experimental stroke) [B. Georgievska et al., *Aberrant sprouting and downregulation of tyrosine hydroxylase in lesioned nigrostriatal dopamine neurons induced by long-lasting overexpression of glial cell line derived neurotrophic factor in the striatum by lentiviral gene transfer, Exp. Neurol.*, 177:461-474 (2002); A. Arvidsson et al., *Elevated GDNF levels following viral vector-mediated gene transfer can increase neuronal death after stroke in rats, Neurobiol. Dis.*, 14:542-556 (2003); C. Rosenblad et al., *Long-term striatal overexpression of GDNF selectively downregulates tyrosine hydroxylase in the intact nigrostriatal dopamine system, Eur. J. Neurosci.*, 17:260-270 (2003)].

The disclosures of all documents referred to throughout this application are incorporated herein by reference. The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other improvements.

One embodiment of the present invention includes a method for treating Parkinson's disease in a mammal, including providing a quantity of a viral vector expressing ShhN and administering a therapeutically effective amount of the quantity of the viral vector to the mammal.

Another embodiment of the present invention includes a method for treating Parkinson's disease in a mammal, including providing a quantity of a viral vector expressing Gli-1 and administering a therapeutically effective amount of the quantity of the viral vector to the mammal.

Another embodiment of the present invention includes a method for protecting dopaminergic nigrostriatal neuronal cell bodies from 6-OHDA-induced neurotoxicity in a mammal, including providing a quantity of a viral vector expressing ShhN and administering a therapeutically effective amount of the quantity of the viral vector to the mammal.

Another embodiment of the present invention includes a method for protecting dopaminergic nigrostriatal neuronal cell bodies from 6-OHDA-induced neurotoxicity in a mammal, including providing a quantity of a viral vector expressing Gli-1 and administering a therapeutically effective amount of the quantity of the viral vector to the mammal.

Another embodiment of the present invention includes a method for treating PD in a mammal, including providing a composition comprising a ShhN protein, a Gli-1 protein, or both, and administering a therapeutically effective amount of the composition to the mammal.

Another embodiment of the present invention includes a method for protecting dopaminergic nigrostriatal neuronal cell bodies from 6-OHDA-induced neurotoxicity in a mammal, including providing a composition comprising a ShhN protein, a Gli-1 protein, or both, and administering a therapeutically effective amount of the composition to the mammal.

Another embodiment of the present invention includes a kit, including a composition comprising a viral vector expressing ShhN, and instructions for its use for treating PD in a mammal.

Another embodiment of the present invention includes a kit, including a composition comprising a viral vector expressing Gli-1, and instructions for its use for treating PD in a mammal.

Another embodiment of the present invention includes a kit, including a composition comprising ShhN protein, Gli-1 protein, or both, and instructions for its use for treating PD in a mammal.

Another embodiment of the present invention includes an in vivo model of nigrostriatal neurodegeneration, comprising a non-human mammal that carries in at least a portion of the cells of its brain at least one exogenous ShhN DNA encoding a ShhN peptide.

Another embodiment of the present invention includes an in vivo model of nigrostriatal neurodegeneration, comprising a non-human mammal that carries in at least a portion of the cells of its brain at least one exogenous Gli-1 DNA encoding a Gli-1 peptide.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures of the drawings. It is intended that the embodiments and figures disclosed herein are to be considered illustrative rather than restrictive.

DETAILED DESCRIPTION

Figure 1:
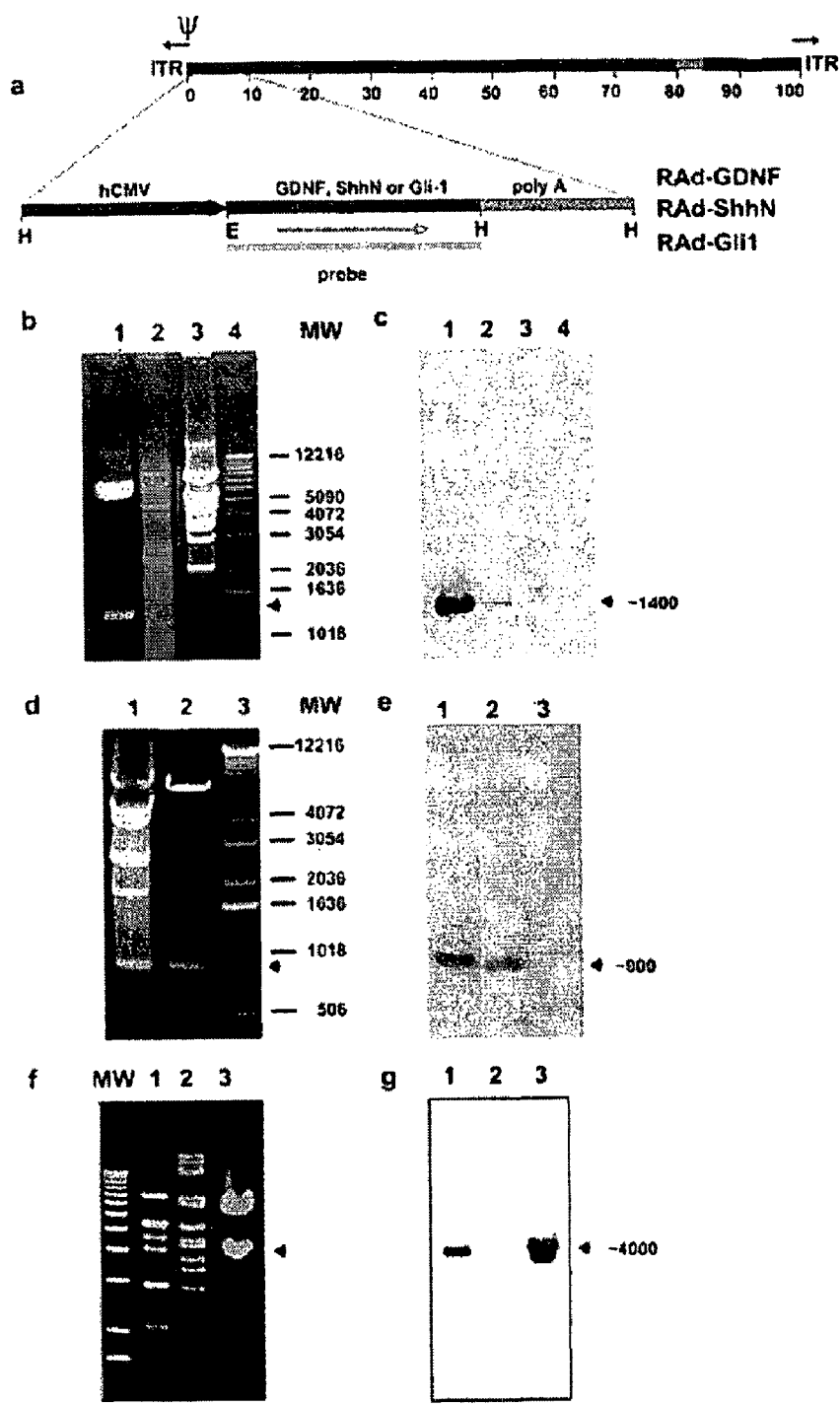
FIG. 1 illustrates the genomic structures of RAd-GDNF, RAd-ShhN, and RAd-Gli-1, in accordance with an embodiment of the present invention. Recombinant adenoviruses (RAd) were generated by homologous recombination after cotransfection into 293 cells of a shuttle expression plasmid encoding ShhN, Gli-1, or Nurr-1 together with the Ad5 genomic plasmid pJM17. The shuttle plasmid contained adenoviral DNA sequences encoding the left-end replication origin/packaging elements and the overlap-recombination region. Restriction patterns of adenoviral vectors digested with HindIII confirmed the presence of the transgenes. Identity of the transgenes was confirmed by Southern blot hybridization, using specific DIG-labeled probes. (a) The schematic structure of the new vectors described herein. (b, c) The characterization of RAd-GDNF, with (b) the restriction analysis and (c) the Southern blot hybridization indicating the presence of the expected transgene band (1.4 kb), in lanes 1 and 2. In b and c the lane numbers indicate 1, the shuttle vector used to construct the recombinant virus, pALGDNF (as positive control); 2, RAd-GDNF; 3, the Ad5 genomic plasmid pJM17 (as negative control); and 4, molecular weight markers. (d, e) The characterization of RAd-ShhN, with (d) the restriction analysis and (e) the Southern blot hybridization indicating the presence of the band containing the transgene ShhN (0.9 kb), in lanes 1 and 2. In d and e the lane numbers indicate 1, RAd-ShhN; 2, the shuttle plasmid pALShhN (as positive control); and 3, molecular weight markers. (f, g) The characterization of RAd-Gli-1, with (f) the restriction analysis and (g) the Southern blot hybridization indicating the presence of the band containing the transgene Gli-1, of approx 4.0 kb, in lanes 1 and 3. In f and g the lane numbers indicate MW, molecular weight markers; 1, RAd-Gli-1; 2, pJM17 (as negative control); and 3, pALGli-1 (as positive control). The construction of Nurr-1 followed identical principles but is not illustrated.

Unless defined otherwise, technical and scientific terms used herein have the same meaning as commonly understood by one of ordinary skill in the art to which this invention belongs. Singleton et al., *Dictionary of Microbiology and Molecular Biology 2nd ed.*, J. Wiley & Sons (New York, N.Y. 1994); March, *Advanced Organic Chemistry Reactions, Mechanisms and Structure 4th ed.*, J. Wiley & Sons (New York, N.Y. 1992); and Sambrook and Russel, *Molecular Cloning: A Laboratory Manual 3rd ed.*, Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" include, but are in no way limited to, lessening or alleviating the severity of Parkinson's disease (PD) or its complications, preventing or inhibiting it from manifesting, preventing or inhibiting it from recurring, merely preventing or inhibiting it from worsening, curing PD, reversing the progression of PD, prolonging a patient's life or life expectancy, ameliorating PD, or a therapeutic effort to effect any of the aforementioned, even if such therapeutic effort is ultimately unsuccessful.

"Curing" PD includes altering the physiology of the central nervous system ("CNS") and/or its biological components to the point that the disease cannot be detected after treatment.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346. Examples of well known vehicles for gene transfer include adenovirus and recombinant adenovirus (RAv), adeno-associated virus (AAV), herpes simplex virus type 1 (HSV-1), and lentivirus (LV).

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Therapeutically effective amount" as used herein refers to that amount which is capable of achieving beneficial results in a patient with PD. A therapeutically effective amount can be determined on an individual basis and will be based, at least in part, on consideration of the physiological characteristics of the mammal, the type of delivery system or therapeutic technique used and the time of administration relative to the progression of the disease:

"Treatment" and "treating," as used herein refer to both therapeutic treatment and prophylactic or preventative measures, wherein the object is to prevent, slow down and/or lessen the disease even if the treatment is ultimately unsuccessful.

"AAV vector" refers to any vector derived from an adeno-associated virus serotype, including, without limitation, AAV-1, AAV-2, AAV-3, AAV-4, AAV-5, AAVX7, etc. AAV vectors can have one or more of the AAV wild-type genes deleted in whole or in part, preferably the Rep and/or Cap genes, but retain functional flanking inverted terminal repeat ("ITR") sequences. Functional ITR sequences are generally necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging. A number of adenovirus-based gene delivery systems have also been developed. Human adenoviruses are double-stranded DNA viruses which enter cells by receptor-mediated endocytosis. These viruses are particularly well suited for gene transfer because they are easy to grow and manipulate and they exhibit a broad host range both in vivo and in vitro. Adenovirus is easily produced at high titers and is stable so that it can be purified and stored. Even in the replication-competent form, adenoviruses generally cause only low level morbidity and are generally not associated with human malignancies. For descriptions of various adenovirus-based gene delivery systems, see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) Bio-Techniques 6:616-629; and Rich et al. (1993) Human Gene Therapy 4:461-476. The construction of recombinant adeno-associated virus ("rAAV") vectors has also been described. See, e.g., U.S. Pat. Nos. 5,173,414 and 5,139,941; International Patent Publication Numbers WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; and Kotin, R. M. (1994) Human Gene Therapy 5:793-801.

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious.

A "recombinant AAV virion" or "rAAV virion" is defined herein as an infectious, replication-defective virus composed of an AAV protein shell, encapsidating a heterologous DNA molecule of interest (e.g., ShhN, Gli-1) which is flanked on both sides by AAV ITRs. A rAAV virion may be produced in a suitable host cell which has had an AAV vector, AAV helper functions and accessory functions introduced therein. In this manner, the host cell is rendered capable of encoding AAV polypeptides that are required for packaging the AAV vector (i.e., containing a recombinant nucleotide sequence of interest) into recombinant virion particles for subsequent gene delivery.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

The term "heterologous," as it relates to nucleic acid sequences such as gene sequences and control sequences, denotes sequences that are not normally joined together and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

"DNA" is meant to refer to a polymeric form of deoxyribonucleotides (i.e., adenine, guanine, thymine and cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine and cytosine, as well as molecules that include base analogues which are known in the art.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences. The boundaries of the gene are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

"Homology" as used herein refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA or two polypeptide sequences are "substantially homologous" to each other when at least about 80%, preferably at least about 90%, and most preferably at least about 95% of the nucleotides or amino acids, respectively, match over a defined length of the molecules, as determined using the methods above.

"Isolated" as used herein when referring to a nucleotide sequence, refers to the fact that the indicated molecule is present in the substantial absence of other biological macromolecules of the same type. Thus, an "isolated nucleic acid molecule which encodes a particular polypeptide" refers to a nucleic acid molecule that is substantially free of other nucleic acid molecules that do not encode the subject polypeptide. However, the molecule may include some additional bases or moieties that do not deleteriously affect the basic characteristics of the composition.

The invention is based on the inventors' study of the activity of the dopaminergic neuron differentiation factor sonic hedgehog (Shh), its downstream transcription factor target Gli-1, and an orphan nuclear receptor, Nurr-1, necessary for the induction of the dopaminergic phenotype of nigrostriatal neurons, in an in vivo model of nigrostriatal neurodegeneration. Experiments demonstrated that all three constructs expressed the proper molecules and that these had the predicted biological activities in vitro. The inventors expressed the N-terminal of sonic hedgehog (ShhN) and the Gli-1 and Nurr-1 entire coding regions from highly purified, and quality controlled, replication-defective adenoviral vectors injected into the brains of rats and used the dopaminergic growth factor GDNF as a positive control. The neurotoxin 6-hydroxydopamine was used to lesion the nigrostriatal dopaminergic innervation. RAd-ShhN and RAd-Gli-1 protected dopaminergic neuronal cell bodies in the substantia nigra, but not axonal terminals in the striatum, from 6-OHDA-induced cell death, while RAd-Nurr-1 was ineffective in protecting either cell bodies or axons. RAd-GDNF was able to protect both the dopaminergic cell bodies and the striatal axon terminals. The inventors' results establish that gene transfer of ShhN and one of its target transcription factors can selectively protect dopaminergic nigrostriatal neuronal cell bodies from a specific neurotoxic insult. Selective protection of nigrostriatal dopaminergic cell bodies by the differentiation factor ShhN and the transcription factor Gli-1 was achieved in a neurotoxic model that eliminates more than 70% of the nigral neurons under consideration. Differentiation and transcription factors can thus be used for the treatment of neurodegeneration by gene therapy.

Shh, secreted by the floor plate, ventralizes the developing neural tube and induces differentiation of midbrain nigrostriatal dopamine neurons [M. Hynes et al., *Induction of midbrain dopaminergic neurons by Sonic hedgehog*, Neuron, 15:35-44 (1995)]. Shh interacts with its receptor patched (ptc) and smoothened (smo) [D. Kalderon, *Transducing the hedgehog signal*, Cell, 103:371-374 (2000)], leading to the phosphorylation and nuclear translocation of the transcription factor Gli-1 [I. A. A. Ruiz et al., *Hedgehog-Gli signalling and the growth of the brain*, Nat. Rev. Neurosci., 3:24-33 (2002); R. J. Hardy, *Dorsoventral patterning and oligodendroglial specification in the developing central nervous system*, J. Neurosci. Res., 50:139-145 (1997)] and activation of downstream genes [C. C. Hui et al., *Expression of three mouse homologs of the Drosophila segment polarity gene cubitus interruptus, Gli; Gli-2, and Gli-3, in ectoderm-and mesoderm-derived tissues suggests multiple roles during postimplantation development*, Dev. Biol., 162:402-413 (1994); J. Lee et al., *Gli1 is a target of Sonic hedgehog that induces ventral neural tube development*, Development, 124:2537-2552 (1997); K. A. Platt et al., *Expression of the mouse Gli and Ptc genes is adjacent to embryonic sources of hedgehog signals suggesting a conservation of pathways between flies and mice*, Mech. Dev., 62:121-135 (1997); H. Sasaki et al., *A binding site for Gli proteins is essential for HNF-3beta floor plate enhancer activity in transgenics and can respond to Shh in vitro*, Development, 124:1313-1322 (1997)].

ShhN protects cultures of fetal dopamine neurons from MPP+ toxicity [N. Miao et al., *Sonic hedgehog promotes the survival of specific CNS neuron populations and protects these cells from toxic insult in vitro*, J. Neurosci., 17:5891-5899 (1997)] and regulates the differentiation and proliferation of neuronal stem cells [K. Lai et al., *Sonic hedgehog regulates adult neural progenitor proliferation in vitro and in vivo*, Nat. Neurosci., 6:21-27 (2003); N. Matsuura et al., *Sonic hedgehog facilitates dopamine differentiation in the presence of a mesencephalic glial cell line*, J. Neurosci., 21:4326-4335 (2001); T. E. Kim et al., *Sonic hedgehog and FGF8 collaborate to induce dopaminergic phenotypes in the Nurr1-overexpressing neural stem cell*, Biochem. Biophys. Res. Commun., 305:1040-1048 (2003)]. Further, Shh peptide injected directly into the brains of rodents and marmosets has beneficial effects in experimental models of PD [E. Bezard et al., *Sonic hedgehog is a neuromodulator in the adult subthalamic nucleus*, FASEB J., 17:2337-2338 (2003); B. Dass et al., *Behavioural and immunohistochemical changes following supranigral administration of sonic hedgehog in 1-methyl-4-phenyl-1,2,3,6-tetrahydropyridine-treated common marmosets*, Neuroscience, 114:99-109 (2002); K. Tsuboi et al., *Intrastriatal injection of sonic hedgehog reduces behavioral impairment in a rat model of Parkinson's disease*, Exp. Neurol., 173:95-104 (2002)]. Nurr-1 is an orphan nuclear receptor necessary for the expression of the dopaminergic phenotype of developing nigrostriatal neurons, such as tyrosine hydroxylase, dopamine transporter [R. H. Zetterstrom et al., *Dopamine neuron agenesis in Nurr1-deficient mice*, Science, 276:248-250 (1997)]. Shh, ptc, smo, Gli-1, and Nurr-1 are present in the adult rodent brain [D. Charytoniuk et al., *Sonic Hedgehog signalling in the developing and adult brain*, J. Physiol. Paris, 96:9-16 (2002); E. Traiffort et al., *Discrete localizations of hedgehog signalling components in the developing and adult rat nervous system*, Eur. J. Neurosci., 11:3199-3214 (1999); E. Traiffort et al., *Regional distribution of Sonic Hedgehog, patched, and smoothened mRNA in the adult rat brain*, J. Neurochem., 70:1327-1330 (1998)].

To test the hypothesis that Shh, Gli-1, or Nurr-1 protects dopamine nigrostriatal neurons from neurotoxin-induced neurodegeneration the inventors constructed RAd vectors expressing ShhN(RAd-ShhN), Gli-1 (RAd-Gli-1), or Nurr-1 (RAd-Nurr-1) under the control of the major immediate early human cytomegalovirus promoter (hCMV) and compared these to GDNF (RAd-GDNF) and a control vector expressing β-galactosidase (RAd-35). RAd-ShhN and RAd-Gli-1 protected nigrostriatal dopaminergic cell bodies, but not their striatal terminals, from 6-OHDA-induced neurodegeneration, while RAd-Nurr-1 was ineffective. These results indicate that nigrostriatal dopaminergic cell bodies can be protected from neurotoxin-induced cell death independent of the maintenance of their axonal terminals. While not wishing to be bound by any particular theory, it is believed that ShhN and Gli-1 may be neuroprotective through the activation of mechanisms different from those of GDNF, which protects both cell bodies and striatal terminals.

In further experimental procedures, the inventors found that neuron-specific expression of Gli-1 using the neuron-specific Tα1 α-tubulin promoter was neuroprotective and its efficiency was comparable to the pancellular strong viral hCMV promoter [D. Suwelack et al., *Neuronal expression of the transcription factor Gli1 using the Tα1 α-tubulin promoter is neuroprotective in an experimental model of Parkinson's disease, Gene Therapy,* 11: 1742-1752 (2004)].

The invention includes compositions and methods for the treatment of PD using ShhN and/or Gli-1, either through gene therapeutic approaches or direct peptide injection. More specifically, the invention includes methods of treating PD by administering a therapeutically effective amount of ShhN and/or Gli-1 to a mammal. In one embodiment of the present invention, the mammal is a human. The ShhN and/or Gli-1 may be formulated into an appropriate pharmaceutical composition for use in connection with the gene therapeutic and/or direct peptide delivery techniques as contemplated by alternate embodiments of the present invention.

The inventive therapeutics may be administered by any appropriate technique, as will be readily appreciated by those of skill in the art. With respect to embodiments of the present invention that incorporate ShhN and/or Gli-1 therapeutics, the therapy may be administered by a gene therapeutic approach. For instance, rAAV virions including heterologous DNA corresponding to a ShhN and/or Gli-1 coding sequence may be generated by any conventional technique known in the art. By way of example, the recombinant AAV virions of the present invention, including the ShhN or Gli-1 DNA of interest, can be produced by a standard methodology that generally involves the steps of: (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient rAAV virion production in the host cell; and (4) culturing the host cell to produce rAAV virions. The AAV vector, AAV helper construct and the helper virus or accessory function vector(s) can be introduced into the host cell either simultaneously or serially, using standard transfection techniques. Examples of such techniques are described in greater detail in the ensuing Examples herein. In accordance with various embodiments of the present invention, it may be particularly beneficial to construct the viral vectors of the instant invention such that ShhN and/or Gli-1 are under the control of, for example, the hCMV promoter or the Tα1 promoter.

AAV vectors are constructed using known techniques to at least provide, as operatively linked components in the direction of transcription, (a) control elements including a transcriptional initiation region, (b) the ShhN and/or Gli-1 DNA of interest and (c) a transcriptional termination region. Moreover, any coding sequence sufficiently homologous to the ShhN and/or Gli-1 coding sequence so as to exhibit functional properties substantially similar to the ShhN and/or Gli-1 coding sequence may be used in connection with alternate embodiments of the present invention. The control elements are selected to be functional in the targeted cell(s). The resulting construct, which contains the operatively linked components, may be bounded (5' and 3') with functional AAV ITR sequences. The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including, without limitation, AAV-1, AAV-2, AAV-3, AAV-4, AAV-5, AAVX7, and the like. Furthermore, 5' and 3' ITRs that flank a selected nucleotide sequence in an AAV expression vector need not necessarily be identical or derived from the same AAV serotype or isolate, so long as they function as intended (i.e., to allow for excision and replication of the bounded ShhN and/or Gli-1 nucleotide sequence of interest).

Therefore, in accordance with an embodiment of the invention, the rAAV virions including a ShhN and/or Gli-1 coding sequence are delivered to a mammal in a sufficient quantity and by a sufficient delivery route so as to effect gene transfer. This may provide an effective treatment for PD in the mammal. In an alternate embodiment of the present invention, this may protect dopaminergic nigrostriatal neuronal cell bodies from 6-OHDA-induced neurotoxicity.

In an alternate embodiment of the present invention, a quantity of ShhN and/or Gli-1 peptide may be directly administered to a mammal in a therapeutically effective amount to treat PD and/or to protect dopaminergic nigrostriatal neuronal cell bodies from 6-OHDA-induced neurotoxicity.

In various embodiments, the present invention provides pharmaceutical compositions (in connection with gene therapeutics and direct peptide administration techniques) including a pharmaceutically acceptable excipient along with either a therapeutically effective amount of a viral vector for delivery of ShhN and/or Gli-1 or a therapeutically effective amount of ShhN and/or Gli-1 protein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. In one embodiment of the present invention the inventive compositions are injected directly into the brain of a mammal.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

The present invention is also directed to a kit for the treatment of PD. The kit is useful for practicing the inventive method of treating PD. The kit is an assemblage of materials or components, including at least one of the inventive compositions. Thus, in some embodiments the kit contains a composition including a viral vector expressing ShhN and/or Gli-1, or, in an alternate embodiment, the kit contains a composition including ShhN and/or Gli-1 peptides, as described above.

The exact nature of the components configured in the inventive kit depends on its intended purpose. For example, some embodiments of the kit are configured for the purpose of treating cultured mammalian cells. Other embodiments are configured for the purpose of treating mammalian cells in vivo (i.e., for treating mammalian subjects in need of treatment, for example, subjects with PD). In one embodiment, the kit is configured particularly for the purpose of treating human subjects.

Instructions for use may be included in the kit. "Instructions for use" typically include a tangible expression describing the technique to be employed in using the components of the kit to effect a desired outcome, such as the treatment of PD. Optionally, the kit also contains other useful components, such as, diluents, buffers, pharmaceutically acceptable carriers, specimen containers, syringes, stents, catheters, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in polynucleotide-based or peptide-based systems. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing nucleic acid or peptide components. The packaging material generally has an external label which indicates the contents and/or purpose of the kit and/or its components.

In another embodiment, the present invention includes various in vivo models of nigrostriatal neurodegeneration, using a non-human mammal that carries in at least a portion of the cells of its brain at least one exogenous ShhN or Gli-1 DNA. Such animal models may be useful for a variety of purposes, including studying a number of diseases and physiologic conditions (e.g., those described herein), as well as screening therapeutic candidates for the treatment of such diseases and physiologic conditions, and still further uses that will be readily apparent to those of skill in the art.

The inventors' experiments demonstrate that the differentiation factor ShhN can act as a trophic factor for embryonic dopaminergic neurons in primary cultures, and, similar to its downstream transcriptional activator, Gli-1, they both protect a significant percentage of adult dopaminergic nigrostriatal neuronal cell bodies from 6-OHDA-induced neurotoxicity. ShhN and Gli-1 protected only the nigral dopaminergic cell bodies from neurodegeneration and not the striatal axonal terminals of these neurons. The positive control vector used expressing GDNF, on the other hand, protected both the nigral cell bodies and the dopaminergic terminals. It is important to note that GDNF protected a higher percentage of nigral cell bodies ($\approx 80\%$) compared to the percentage of striatal dopaminergic innervation ($\approx 60\%$). The inventors' negative control vector expressing the reporter β-galactosidase and the RAd-Nurr-1 vector, however, were unable to protect either the cell bodies or the dopaminergic axon terminals in the striatum. The use of internal positive and negative control vectors provided stringent mechanisms to identify both active and inactive factors able to protect nigral cell bodies from neurotoxic degeneration.

6-OHDA reduced the size of dopaminergic neuronal cell bodies in the substantia nigra. RAd-GDNF, which showed the greatest capacity to maintain the axonal terminals of nigrostriatal neurons, also achieved the greatest protection of cell body size in the substantia nigra. While ShhN and Gli-1 were less potent, they significantly protected against the neurotoxin-induced soma atrophy. Thus, while GDNF was more effective in preserving nigral dopamine neuron numbers, striatal tyrosine hydroxylase axon terminal density, and nigral dopamine soma size, ShhN and Gli-1 had a protective effect on neuronal numbers and nigral soma area, but were completely ineffective in protecting the striatal dopaminergic innervation from neurotoxin-induced degeneration. Thus, ShhN and Gli-1 protected partially against the denervation-induced soma atrophy, without preserving the density of dopaminergic striatal innervation.

Administration of GDNF into the substantia nigra has been previously been shown to protect mainly the nigral dopaminergic cell bodies [A. Bjorklund et al., *Towards a neuroprotective gene therapy for Parkinson's disease: use of adenovirus, AAV and lentivirus vectors for gene transfer of GDNF to the nigrostriatal system in the rat Parkinson model, Brain Res.*, 886:82-98 (2000)] but not the striatal axonal terminals. Delivery of GDNF to the striatum has been shown to provide neuroprotection to both nigral cell bodies and axonal terminals, as seen in the experiments performed and described herein and those described by others [D. L. Choi-Lundberg et al., *Dopaminergic neurons protected from degeneration by GDNF gene therapy, Science*, 275:838-841 (1997); A. Bjorklund et al., *Towards a neuroprotective gene therapy for Parkinson's disease: use of adenovirus, AAV and lentivirus vectors for gene transfer of GDNF to the nigrostriatal system in the rat Parkinson model, Brain Res.*, 886:82-98 (2000); D. L. Choi-Lundberg et al., *Behavioral and cellular protection of rat dopaminergic neurons by an adenoviral vector encoding glial cell line-derived neurotrophic factor, Exp. Neurol.*, 154: 261-275 (1998); B. Connor et al., *Differential effects of glial cell line-derived neurotrophic factor (GDNF) in the striatum and substantia nigra of the aged Parkinsonian rat, Gene Ther.*, 6:1936-1951 (1999); B. Connor et al., *Glial cell line-derived neurotrophic factor (GDNF) gene delivery protects dopaminergic terminals from degeneration, Exp. Neurol.*, 169:83-95 (2001)]. Further, the anti-apoptotic protein XIAP has also been shown to protect predominantly nigral cell bodies upon delivery using recombinant adenovirus into the striatum of mice [O. Eberhardt et al., *Protection by synergistic effects of adenovirus-mediated X-chromosome-linked inhibitor of apoplosis and glial cell line-derived neurotrophic factor gene transfer in the 1-methyl-4-henyl-1,2,3,6-tetrahydropyridine model of Parkinson's disease, J. Neurosci.*, 20:9126-9134 (2000)]. Thus, there is precedence for the selective neuroprotection of nigral dopaminergic cell bodies, even when using experimental paradigms comparable to those described herein.

The increased effectiveness of GDNF may be related to its capacity to preserve the striatal axon terminals [B. Connor et al., *Differential effects of glial cell line-derived neurotrophic factor (GDNF) in the striatum and substantia nigra of the aged Parkinsonian rat, Gene Ther.*, 6:1936-1951 (1999); A. Bilang-Bleuel et al., *Intrastriatal injection of an adenoviral vector expressing glial-cell-line-derived neurotrophic factor prevents dopaminergic neuron degeneration and behavioral impairment in a rat model of Parkinson disease, Proc. Natl. Acad. Sci. USA*, 94:8818-8823 (1997)]. Although recently untoward effects of GDNF have been described at long times following GDNF delivery [B. Georgievska et al., *Aberrant sprouting and downregulation of tyrosine hydroxylase in lesioned nigrostriatal dopamine neurons induced by long-lasting overexpression of glial cell line derived neurotrophic factor in the striatum by lentiviral gene transfer, Exp. Neurol.*, 177:461-474 (2002); C. Rosenblad et al, *Long-term striatal overexpression of GDNF selectively downregulates tyrosine hydroxylase in the intact nigrostriatal dopamine system, Eur. J. Neurosci.*, 17:260-270 (2003)], the experimental design upon which the present invention is based was not designed to examine these specifically, and thus, they were not uncovered. Intrastriatal 6-OHDA causes a slow degeneration of nigral neurons. Hence, although not wishing to be bound by any particular theory, it is believed that nigral neuron survival could depend on the continued retrograde transport of the adenoviruses, or the growth factors encoded by them, to the substantia nigra. It has been recently demonstrated that Shh and its receptor Ptc can also be endocytosed in neural plate explants; suggesting that this event may be linked to the mechanism of Shh signal transduction [J. P. Incardona et al, *Receptor-mediated endocytosis of soluble and membrane-tethered Sonic hedgehog by Patched-1, Proc. Natl. Acad. Sci. USA*, 97:12044-12049 (2000)]. These mechanisms will operate only in the presence of intact axon terminals, and the loss of striatal axons will thus compromise the effectiveness of RAd-ShhN and RAd-Gli-1. Retrograde transport of RAds has been demonstrated by the inventors in this paradigm and has also been described by others [D. L. Choi-Lundberg et al., *Behavioral and cellular protection of rat dopaminergic neurons by an adenoviral vector encoding glial cell line-derived neurotrophic factor, Exp. Neurol.*, 154:261-275 (1998); V. Ridoux et al, *Adenoviral vectors as functional retrograde neuronal tracers, Brain Res.*, 648:171-175 (1994)].

Nurr-1, despite being indispensable during early brain development for the expression of the dopaminergic phenotype [R. H. Zetterstrom et al, *Dopamine neuron agenesis in Nurr1-deficient mice, Science*, 276:248-250 (1997)], had no effect on the survival of nigral dopamine neurons in the inventors' experimental paradigm. Nurr-1 is a powerful factor that contributes to the determination of the dopaminergic phenotype during neuronal differentiation, most possibly by heterodimerization with the retinoid X receptor [A. Wallen-Mackenzie et al, *Nurr1-RXR heterodimers mediate RXR ligand-induced signaling in neuronal cells, Genes Dev.*, 17.3036-3047 (2003)]. Thus, Nurr-1 activates dopaminergic-specific genes in neuronal stem cells, and allows the differentiation of neuronal stem cells along a dopaminergic pathway, and has also been shown to have a neuroprotective effect in mouse neural stem cells [K. Sakurada et al, *Nurr1, an orphan nuclear receptor, is a transcriptional activator of endogenous tyrosine hydroxylase in neural progenitor cells derived from the adult brain, Development*, 126:4017-4026 (1999); T. E. Kim et al, *Sonic hedgehog and FGF8 collaborate to induce dopaminergic phenotypes in the Nurr1-overexpressing neural stem cell, Biochem. Biophys. Res. Commun.*, 305:1040-1048 (2003); J. Wagner et al., *Induction of a midbrain dopaminergic phenotype in Nurr1-overexpressing neural stem cells by type 1 astrocytes, Nat. Biotechnol.*, 17:653-659 (1999); J. Y. Kim et al., *Dopaminergic neuronal differentiation from rat embryonic neural precursors by Nurr1 overexpression, J. Neurochem.*, 85:1443-1454 (2003); J. Satoh et al., *The constitutive and inducible expression of Nurr1, a key regulator of dopaminergic neuronal differentiation, in human neural and non-neural cell lines, Neuropathology*, 22:219-232 (2002); M. A. Lee et al., *Overexpression of midbrain-specific transcription factor Nurr1 modifies susceptibility of mouse neural stem cells to neurotoxins, Neurosci. Lett.*, 333:74-78 (2002)]. In summary, the role of Nurr-1 in promoting the development of the dopaminergic phenotype of midbrain neurons has been studied during ontogenesis, but its role in adults has not been thoroughly evaluated. That it does play a role can be surmised by its being essential for the expression of Ret, a central component of GDNF signaling, in midbrain dopamine neurons [A. A. Wallen et al., *Orphan nuclear receptor Nurr1 is essential for Ret expression in midbrain dopamine neurons and in the brain stem, Mol. Cell. Neurosci.*, 18:649-663 (2001)]. Thus, the lack of effect of Nurr-1 could be due to the high constitutive levels of Nurr-1 already present in the adult brain, its exclusive cell-autonomous function, or its lack of neuroprotective action against neurotoxins [R. H. Zetterstrom et al., *Retinoid X receptor heterodimerization and developmental expression distinguish the orphan nuclear receptors NGFI-B, Nurr1, and Nor1*, Mol. Endocrinol., 10:1656-1666 (1996); R. H. Zetterstrom et al., *Cellular expression of the immediate early transcription factors Nurr1 and NGFI-B suggests a gene regulatory role in several brain regions including the nigrostriatal dopamine system*, Brain Res. Mol. Brain. Res., 41:111-120 (1996)].

Previously, GDNF has been successfully used in several animal models of PD [M. C. Bohn, *A commentary on glial cell line-derived neurotrophic factor (GDNF): from a glial secreted molecule to gene therapy*, Biochem. Pharmacol., 57:135-142 (1999)]. However, in a clinical trial, intraventricular administration of GDNF protein failed to prevent nigrostriatal degeneration [J. H. Kordower et al., *Clinicopathological findings following intraventricular glial-derived neurotrophic factor treatment in a patient with Parkinson's disease*, Ann. Neurol., 46:419-424 (1999)]; it did not improve parkinsonism, and side effects including weight loss, paresthesias, and hyponathremia were reported [J. G. Nutt et al., *Randomized, double-blind trial of glial cell line-derived neurotrophic factor (GDNF) in PD*, Neurology, 60:69-73 (2003)]. In a more recent clinical trial in which GDNF was injected directly into the affected striatum of PD patients, potentially therapeutic results were forthcoming [S. S. Gill et al., *Direct brain infusion of glial cell line-derived neurotrophic factor in Parkinson disease*, Nat. Med., 9:589-595 (2003)]. This indicates that direct delivery of neuronal growth factors into target brain areas may be effective in human patients. Methods such as gene therapy, by providing sustained and regulated growth factor, may thus become the delivery method of choice for the treatment of PD.

There has been one previous report suggesting that ShhN peptide protected DA neurons in primary cultures from MPP+-induced neurodegeneration [N. Miao et al., *Sonic hedgehog promotes the survival of specific CNS neuron populations and protects these cells from toxic insult in vitro*, J. Neurosci., 17:5891-5899 (1997)]. More recently, ShhN peptide has been proposed to act as a neuromodulator in the adult subthalamic nucleus [E. Bezard et al., *Sonic hedgehog is a neuromodulator in the adult subthalamic nucleus*, FASEB J., 17:2337-2338 (2003)] and to protect partially from 6-OHDA-induced neurotoxicity in rodents [K. Tsuboi et al., *Intrastriatal injection of sonic hedgehog reduces behavioral impairment in a rat model of Parkinson's disease*, Exp. Neurol., 173:95-104 (2002)] and marmosets [B. Dass et al., *Behavioural and immunohistochemical changes following supranigral administration of sonic hedgehog in 1-methyl-4-phenyl-1,2,3,6-tetrahydropyridine-treated common marmosets*, Neuroscience, 114:99-109 (2002)]. However, the inventors are the first to describe that, in vivo, ShhN or the transcription factor downstream of Shh signaling, Gli-1, expressed by a recombinant viral gene transfer vector, protects dopaminergic nigrostriatal neurons from neurodegeneration. In the inventors' experiments, RAd-GDNF was more effective than either RAd-ShhN or RAd-Gli-1, similar to results obtained when ShhN peptide was injected directly into the striatum and compared to infused GDNF [K. Tsuboi et al., *Intrastriatal injection of sonic hedgehog reduces behavioral impairment in a rat model of Parkinson's disease*, Exp. Neurol., 173:95-104 (2002)].

In the inventors' experiments, RAd-ShhN or RAd-Gli-1 protected a significant percentage of dopaminergic nigrostriatal neurons from neurodegeneration; although behavioral protection could not be detected with RAd-GDNF, RAd-ShhN, or RAd-Gli-1, because the inventors could not detect any rotational asymmetries in response to the lesion. Thus, the experimental model did not allow for the testing for any behavioral protection and is thus a model of neuroanatomical neuroprotection (data not shown). This correlated with the lack of neuroprotection of striatal dopaminergic terminals, since behavioral neuroprotection of striatal function is contingent on the preservation of the dopaminergic striatal innervation. However, it was recently reported that ShhN peptide injected directly into the striatum prevented behavioral modifications induced by 6-OHDA and protected some of the dopaminergic innervation density, but was less powerful compared to GDNF [K. Tsuboi et al., *Intrastriatal injection of sonic hedgehog reduces behavioral impairment in a rat model of Parkinson's disease*, Exp. Neurol., 173:95-104 (2002)]. Different results obtained by both groups could be explained by the repeated and presumably higher doses of ShhN peptide injected directly into the striatum [K. Tsuboi et al., *Intrastriatal injection of sonic hedgehog reduces behavioral impairment in a rat model of Parkinson's disease*, Exp. Neurol., 173:95-104 (2002)] and/or other experimental differences between both sets of experiments.

Differences in the effectiveness between GDNF and ShhN/Gli-1 could be attributed to differences in the density of receptors and signaling pathways activated by either factor. The receptors for ShhN, Ptc and Smo, have been identified in the adult rat brain in several regions, including striatum and midbrain [E. Traiffort et al., *Regional distribution of Sonic Hedgehog, patched, and smoothened mRNA in the adult rat brain*, J. Neurochem., 70:1327-1330 (1998)]. However, the density of these receptors in the adult brain has not been determined: For GDNF, however, it is clear that its receptors are expressed at physiologically relevant levels in the adult brain of various species, including human [A. Josephson et al., *GDNF and NGF family members and receptors in human fetal and adult spinal cord and dorsal root ganglia*, J. Comp. Neurol., 440:204-217 (2001); T. C. Burazin et al., *Localization of GDNF/neurturin receptor (c-ret, GFRalpha-1 and alpha-2) mRNAs in postnatal rat brain: differential regional and temporal expression in hippocampus, cortex and cerebellum*, Brain Res. Mol. Brain. Res., 73:151-171 (1999); J. P. Golden et al., *Expression of neurturin, GDNF, and GDNF family-receptor mRNA in the developing and mature mouse*, Exp. Neurol., 158:504-528 (1999); J. P. Golden et al., *Expression of neurturin, GDNF, and their receptors in the adult mouse CNS*, J. Comp. Neurol., 398:139-150 (1998); G. Paratcha et al., *The neural cell adhesion molecule NCAM is an alternative signaling receptor for GDNF family ligands*, Cell, 113:867-879 (2003)].

Although not wishing to be bound by any particular theory, it is believed that differences in signaling pathways activated by GDNF or ShhN/Gli-1 most likely explain their different activities. GDNF signals through binding to GRF1α and its interactions with the Ret-receptor tyrosine kinase. The expression of GRF1α is regulated by TGFβ, and ret is, under the control of Nurr-1 [A. A. Wallen et al., *Orphan nuclear receptor Nurr1 is essential for Ret expression in midbrain dopamine neurons and in the brain stem*, Mol. Cell. Neurosci., 18:649-663 (2001); H. Sariola et al., *Novel functions and signalling pathways for GDNF*, J. Cell Sci., 116 Pt. 19:3855-3862 (2003); M. S. Airaksinen et al., *The GDNF family: signalling, biological functions and therapeutic value*, Nat. Rev. Neurosci., 3:383-394 (2002)]. More recently, it has also been demonstrated that GDNF can bind to heparan sulfate proteoglycans to activate the Met-receptor tyrosine kinase or bind to NCAM, leading to the activation of Fyn and FAK. The rescuing of nigrostriatal neurons from neurotoxin-induced toxicity has not yet been linked to individual signaling pathways.

Shh signals through its interactions with Ptc and Smo, leading to the activation of a macromolecular complex consisting of Suppressor of fused, Fused, and protein kinase A, which phosphorylates and activates Gli proteins [I. A. A. Ruiz et al., *Hedgehog-Gli signalling and the growth of the brain, Nat. Rev. Neurosci.*, 3:24-33 (2002)]. Although the overall signaling pathways are not completely elucidated in the CNS, the inventors' data suggest that Gli-1 is downstream of Shh signaling.

Thus, the inventors have demonstrated that a single intrastriatal injection of a RAd encoding ShhN or its downstream transcriptional activator Gli-1 protects dopamine neurons against 6-OHDA neurotoxicity in vivo and also protected these cells from neurotoxin-induced cell body atrophy. Nevertheless, this treatment did not prevent the dopaminergic denervation of the striatum. This demonstrates the feasibility of using transcriptional gene therapy to mimic neuroprotective signals to bypass any limited availability of receptors or signaling cascades of neurotrophic factors. This strategy may be used both in the context of therapeutic applications and to determine which signaling pathway mediates particular effects of a given neurotrophic factor. The experimental results suggest that adenovirus-mediated gene transfer using Shh or downstream elements of its signaling pathways represents a new strategy to prevent progressive degeneration of dopamine-containing neurons in the substantia nigra in disorders such as PD.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention

Example 1

Preparation of Cell Lines

Human embryonic kidney cells (293 transformed with E1 from Ad5) were obtained from Microbix, Biosystems Inc. (Toronto, Ontario; Canada); HeLa and BHK cells were purchased form the European Collection of Animal Cell Cultures (Porton Down, Salisbury; UK). These cells were grown using complete minimal essential medium Eagle (MEM; fetal bovine serum 10%, penicillin/streptomycin 1%, L-glutamine 1%, MEM nonessential amino acids) and incubated at 37° C. with 5% $CO_2$ [P. Lowenstein et al., *Protocols for Gene Transfer in Neuroscience. Towards Gene Therapy of Neurological Disorders*, Wiley, Chichester (1996)]. C3H/10T1/2 cells, a mouse embryo mesenchymal cell line that can be differentiated into cartilage and bone, were used to test the bioactivity of ShhN and Gli-1. Differentiation induces alkaline phosphatase expression detected histochemically. C3H/10T1/2 cells were grown in basal Eagle medium with Earle's BSS 90%, supplemented with 10% heat-inactivated fetal bovine serum in 25-$cm^2$ flasks and incubated at 37° C. with 5% $CO_2$ and passaged at 60% confluency.

Example 2

Preparation of Ventral-Mesencephalic Primary Cultures

Pregnant Sprague-Dawley rats were killed by neck dislocation on day E14.5 [K. Shimoda et al., *A high percentage yield of tyrosine hydroxylase-positive cells from rat E14 mesencephalic cell culture, Brain Res.*, 586:319-331 (1992)]. The uterus was removed and transferred to ice-cold buffer, where fetuses were removed until dissection under a stereomicroscope as described in detail elsewhere [K. Shimoda et al., *A high percentage yield of tyrosine hydroxylase-positive cells from rat E14 mesencephalic cell culture, Brain Res.*, 586:319-331 (1992); A. F. Shering et al., *Cell type-specific expression in brain cell cultures from a short human cytomegalovirus major immediate early promoter depends on whether it is inserted into herpesvirus or adenovirus vectors, J. Gen. Virol.*, 78:445-459 (1997)]. Neocortical cultures were prepared as described earlier [A. F. Shering et al., *Cell type-specific expression in brain cell cultures from a short human cytomegalovirus major immediate early promoter depends on whether it is inserted into herpesvirus or adenovirus vectors, J. Gen. Virol.*, 78:445-459 (1997)], and midbrain cultures were prepared as in Shimoda et al. [K. Shimoda et al., *A high percentage yield of tyrosine hydroxylase-positive cells from rat E14 mesencephalic cell culture, Brain Res.*, 586:319-331 (1992)]. Glial cells from the neocortical cultures were immunostained with antibodies against glial fibrillary acidic protein, and ventral-mesencephalic (VM) midbrain cultures were shown to be enriched in dopaminergic neurons by immunostaining with antibodies to tyrosine hydroxylase.

Serum-containing or serum-free media were prepared as follows. Serum-free medium consisted of Dulbecco's modified Eagles medium (DMEM)-F12 (1:1; obtained from Life Technologies) containing 2 mM L-glutamine (obtained from Life Technologies), 100 units of penicillin/ml, 100 units of streptomycin/ml (obtained from Life Technologies), 33 mM glucose (obtained from Sigma), and the N1 supplements [5 µg/ml insulin (obtained from Sigma), 5 µg/ml transferrin (obtained from Sigma), $2\times10^{-8}$ M progesterone (obtained from Sigma), 100 µM putrescine (obtained from Sigma), and $3\times10^{-8}$ M selenium (as $Na_2SeO_3$) (obtained from Sigma)]. Serum containing medium was DMEM-F12 (1:1; obtained from Life Technologies) containing 10% fetal bovine serum (obtained from Life Technologies), 4.0 mM glutamine (obtained from Life Technologies), 100 units of penicillin/ml, and 100 units of streptomycin/ml (obtained from Life Technologies). To prepare conditioned media (CM) from either BHK cells or glial cultures, cells were infected for 6 hours with an m.o.i. of 300 for each virus and then incubated for a further 48 hours. At this time medium was removed, centrifuged, and filtered with a 0.2-µm Sartorius filter. Conditioned medium was diluted 1:1 in fresh medium to maintain cell viability.

Example 3

Construction of Recombinant Adenovirus

The cDNA encoding Shh amino-terminal gene product was excised by enzymatic digestion with EcoR1/HindIII from a recombinant pBluescript II plasmid provided by Dr. P. Beachy, John Hopkins University (Baltimore, Md.). The full-length (3.6 kb) HindIII/XbaI insert of human (*Homo sapiens*) Gli-1 cDNA clone pGLIK12 was kindly provided by Dr. Bert Volgestein, Johns Hopkins University, and the full-length (0.7 kb) BamHI/XhoI insert of rat GDNF cDNA clone pCDNA-GDNF was made available by Dr. Ira Black (UM-DNJ, NJ). These inserts were then cloned into the shuttle vector pAL119, yielding pALShhN, pALGli-1, and pAL-GDNF containing the ShhN, the Gli-1, or the GDNF coding region, respectively, in the sense orientation with respect to the major immediate early hCMV promoter of pAL119 [A. F. Shering et al., *Cell type-specific expression in brain cell cultures from a short human cytomegalovirus major immediate early promoter depends on whether it is inserted into herpesvirus or adenovirus vectors, J. Gen. Virol.*, 78:445-459 (1997)]. The orientation of the cloned transgenes was determined by restriction analysis with EcoRI or HindIII for ShhN and HindIII or SacI for Gli-1 [M. M. Hitt et al., *Human adenovirus vectors for gene transfer into mammalian cells, Adv. Pharmacol.*, 40:137-206 (1997)]. Recombinant adenoviruses RAd-ShhN, RAd-Gli-1, and RAd-GDNF expressing ShhN, Gli-1, and GDNF, respectively, under the control of the major immediate early hCMV promoter were generated by cotransfection of the shuttle plasmid pALShhN, pALGli-1, or pALGDNF with the Ad5 genomic plasmid pJM17 into 293 HEK cells as earlier described [P. Lowenstein et al., *Protocols for Gene Transfer in Neuroscience. Towards Gene Therapy of Neurological Disorders*, Wiley, Chichester (1996); A. F. Shering et al., *Cell type-specific expression in brain cell cultures from a short human cytomegalovirus major immediate early promoter depends on whether it is inserted into herpesvirus or adenovirus vectors, J. Gen. Virol.*, 78:445-459 (1997); T. Southgate et al., *Gene transfer into neural cells in vivo using adenoviral vectors*, In: C. R. Gerfen, R. McKay, M. A. Rogawski, D. R. Sibley and P. Skolnick, Editors, *Current Protocols in Neuroscience*, Wiley, New York (2000), 4.23.1-4.23.40]. After molecular characterization of the RAds, they were purified by three rounds of dilution limiting assay, scaled up, and purified by $CsCl_2$ gradient, and the presence and identity of the transgenes were confirmed by restriction and Southern blot analysis.

The construction and use of RAd-35 (expressing β-galactosidase) and RAd-TK (expressing HSV-1 TK), both under the control of the hCMV promoter, were described earlier [R. A. Dewey et al., *Chronic brain inflammation and persistent herpes simplex virus 1 thymidine kinase expression in survivors of syngeneic glioma treated by adenovirus-mediated gene therapy implications for clinical trials, Nat. Med.*, 5:1256-1263 (1999); A. J. Zermansky et al., *Towards global and long-term neurological gene therapy unexpected transgene dependent, high-level, and widespread distribution of HSV-1 thymidine kinase throughout the CNS, Mol. Ther.*, 4:490-498 (2001); A. F. Shering et al., *Cell type-specific expression in brain cell cultures from a short human cytomegalovirus major immediate early promoter depends on whether it is inserted into herpesvirus or adenovirus vectors, J. Gen. Virol.*, 78:445-459 (1997)]. Quality control of viral stocks was assayed by detection of contaminating replication-competent adenovirus (RCA) [L. D. Dion et al., *Supernatant rescue assay vs. polymerase chain reaction for detection of wild type adenovirus-contaminating recombinant adenovirus stocks, J. Virol. Methods*, 56:99-107 (1996)] or endotoxin (LPS), using the Multitest Limulus Amebocyte Lysate Pyrogen Kit (obtained from Biowhittaker, Inc.). All viral stocks used in the study were RCA and LPS free [T. Southgate et al., *Adenoviral vectors for gene transfer into neural cells in primary culture*, In: D. Sibley, Editor, *Current Protocols in Neuroscience*, Wiley, New York (2000), 4.23.1-4.23.40].

Example 4

Analysis of Shh Expression and Secretion

The expression and secretion of ShhN into the culture medium after infection of BHK cells with RAd-ShhN was evaluated by dot blot, Western blot, and ELISA. edia from RAd-infected cells (i.e., CM), were prepared as described above. For dot-blot analysis, 200 µl of CM from uninfected or RAd-ShhN or RAd-35-infected BHK cells was bound to nitrocellulose membrane (Hybond ECL; obtained from Amersham Pharmacia Biotech) using a Bio-Dot apparatus (obtained from Bio-Rad), and the nitrocellulose membrane was probed using the 5E1 anti-ShhN monoclonal antibody (1:1000 [J. Ericson et al., *Two critical periods of Sonic Hedgehog signaling required for the specification of motor neuron identity, Cell*, 87:661-673 (1996)]) as primary antibody and biotinylated anti-mouse antibody (1:1000; obtained from DAKO) as secondary antibody. Colorimetric detection of Shh immunoreactivity was carried out using the biotin-avidin-horseradish peroxidase detection kit (Vectastain ABC; obtained from Vector Laboratories). For Western blot analysis, CM from uninfected or RAd-35 or RAd-ShhN-infected BHK cells was concentrated 25-fold using an Ultrafree-0.5 centrifugal kit (obtained from Millipore) (Biomax 5-kDa NMWL-membrane). Concentrated CM samples were fractionated by Nu-PAGE and transferred to a nitrocellulose membrane (Hybond ECL; obtained from Amersham Pharmacia Biotech) for 30 minutes at 15 V using a semidry blot transfer system (obtained from Hoeffer Scientific Instruments). The membrane was probed using a specific goat anti-ShhN polyclonal antibody (1:100; obtained from Santa Cruz Biotechnology, Inc.) as primary antibody and a biotinylated anti-goat antibody (1:1000; obtained from DAKO) as secondary antibody. Colorimetric detection of ShhN was carried out using an ABC detection kit (obtained from Vector Laboratories). ELISA was carried out as follows: 96-well ELISA plates (obtained from Greiner) were coated with 50 µl of coating solution (coating antibody Shh 5E1 [J. Ericson et al., *Two critical periods of Sonic Hedgehog signaling required for the specification of motor neuron identity, Cell*, 87:661-673 (1996)] diluted 1:500 in PBS, pH 7.2) overnight at room temperature. Coating solution was discarded the next day. Nonspecific binding sites were blocked by incubating with 100 µl of 3% BSA-PBS solution for 2 hours at 37° C. The plate was then washed three times with 0.2% Tween 20-PBS solution. Conditioned medium from RAd-infected BHK cells (100 µl/well) was added to the plate and incubated at 37° C. for 2 hours. After the incubation period, the plate was washed three times using a 0.1% Tween 20-PBS solution. The plate was then incubated with 50 µl/well of secondary antibody (goat anti-Shh polyclonal antibody diluted 1:200 in 3% BSA-PBS solution) for 1 hour at room temperature and washed, and 35 µl of detection antibody [anti-goat biotinylated antibody (obtained from DAKO) diluted 1:5000 in 3% BSA-PBS solution] was added to each well. The plate was then incubated for another hour at room temperature and washed thoroughly to remove any remaining unbound antibody. The plate was incubated with 100 µl of ABC (obtained from Vector Laboratories) for 30 minutes and washed. Finally, 100 µl of 1 mg/ml ABTS substrate (obtained from Sigma) was added. The reaction was developed in the dark for 30 minutes at room temperature. The presence of ShhN in conditioned medium was determined by reading the absorbance at 405 nm.

Example 5

In Vitro Assessment of ShhN-Mediated Survival of Dopaminergic Midbrain Neurons

To assay ShhN-mediated survival of dopaminergic neurons, VM cell primary cultures were plated and maintained in 50% conditioned medium from infected and control BHK cells for 7 or 4 days, respectively. VM primary culture cells were then fixed with 4% paraformaldehyde and 0.2 M sucrose in PBS, pH 7.4, and processed for tyrosine hydroxylase (TH) immunocytochemistry. The number of TH-positive cells present in each condition was counted. To confirm the specific effects of ShhN on dopaminergic neuron survival, an immunoblocking experiment was performed by adding to the conditioned medium from mock-, RAd-35-, or RAd-ShhN-treated BHK cells the 5E1 anti-ShhN antibody (to a final dilution of 1:500 [J. Ericson et al., *Two critical periods of Sonic Hedgehog signaling required for the specification of motor neuron identity, Cell*, 87:661-673 (1996)]) for 30 minutes at 4° C. before addition of the mixture to VM cultures. VM cultures were incubated for four further days after which they were processed for TH immunocytochemistry using the ABC kit. The number of TH-immunoreactive neurons was counted using a total magnification of 200×. Data regarding the survival of dopaminergic neurons in culture, as well as ShhN-blocking experiments, were confirmed in three independent experiments in triplicate, values were expressed as means±SEM, and differences in the survival of TH-immunoreactive neurons among the treatments were analyzed statistically [R. Sokal, *The Principles and Practice of Statistics in Biological Research*, vol. 2, W.H. Freeman, Oxford (1981)]. Differences in TH+ neuronal survival were evaluated by the Student t test. The differences between the effects of each treatment were assessed by one-way ANOVA. When the ANOVA showed significant differences, pair-wise comparisons between means were tested using either Tukey or Dunnett multiple comparisons test [R. Sokal, *The Principles and Practice of Statistics in Biological Research*, vol. 2, W.H. Freeman, Oxford (1981)]. Statistical tests were performed using the SPSS statistical package for Windows version 9 (obtained from SPSS, Inc.).

Example 6

In Vitro Bioactivity of RAd-ShhN, RAd-Gli-1, and RAd-Nurr-1, Determined as ShhN- or Gli-1-Induced Differentiation of C3H10T1/2 cells or Nurr-1-Induced Luciferase Expression from a Nurr-1-Responsive Promoter Differentiation of the pluripotential cell line C3H10T1/2 into the osteoblastic lineage in response to RAd-ShhN or RAd-Gli-1 infection was carried out as follows: $1 \times 10^5$ cells per well were seeded in two six-well plates and later infected with either RAd-ShhN or RAd-Gli-1 at m.o.i. 200. Uninfected cells or a control adenovirus (RAd-35; m.o.i. 200) was used as negative control. The induction of osteoblast phenotype in response to the viral treatment was determined by detecting alkaline phosphatase (AP) activity, a marker of bone differentiation, using the histochemical detection afforded by the kit Fast Red TR/Naphtol AS-MX (obtained from Sigma). AP-positive cells (red reaction product) in each well were visualized under light microscopy and three independent experiments were carried out to confirm the results. To test the bioactivity of RAd-Nurr-1, a COS-7 cell line transiently transfected with a plasmid containing a specific Nurr-1-responsive element, NBRE-LUC (kindly provided by Dr. J. Milbrandt), and thus responding to the presence of Nurr-1 with an increase in luciferase activity was used.

Example 7

Detection of TH Immunoreactivity by Immunohistochemistry

Midbrain cultures or brain sections were permeabilized in 2 ml of TBS/Triton X-100 (0.5% v/v) at room temperature and washed, and endogenous peroxidase activity was inactivated by adding 3 ml of 0.3% $H_2O_2$ for 15 minutes. Nonspecific antibody binding sites and Fc receptors were blocked by incubating the sections with 10% horse serum (HS) in 1 ml of TBS/Triton for 1 hour and washed, and sections were incubated with a specific rabbit anti-TH polyclonal antibody (obtained from Pharmingen) diluted 1:1000 in TBS/Triton/1% HS. This incubation was carried out overnight at room temperature. Sections were then washed and incubated for 4 hours with rabbit biotinylated secondary antibody (1:200) in TBS/Triton/1% horse serum. TH immunoreactivity was revealed using ABC (obtained from Vector Laboratories), and diaminobenzidine tetrahydrochloride (obtained from Sigma) was the substrate for horseradish peroxidase. Sections were washed, mounted onto gelatin-coated slides, air-dried, dehydrated, and cover-slipped with DPX as previously described [C. E. Thomas et al., *Gene transfer into rat brain using adenoviral vectors*, In: J. N; Gerfen, R. McKay, M. A. Rogawski, D. R. Sibley and P. Skolnick, Editors, *Current Protocols in Neuroscience*, Wiley, New York (2000), 4.23.1-4.23.40].

Example 8

Immunocytochemical Detection of β-Galactosidase, HSV-1 TK, ShhN, Gli-1, and Nurr-1

The striatum or substantia nigra of animals injected with RAd-35, RAd-TK, RAd-ShhN, RAd-Gli-1, or RAd-Nurr-1 was immunostained as described in detail above. ShhN was detected using a mouse monoclonal antibody raised against the amino-terminal of Shh (obtained from University of Iowa Hybridoma Bank), Gli-1 and Nurr-1 were detected using rabbit polyclonal antibodies raised against the amino-terminal of Gli-1 or against Nurr-1 (obtained from Santa Cruz Biotechnology). HSV-1 TK was detected with a specific polyclonal rabbit antibody raised against a TK-specific peptide and produced by the inventors and published elsewhere [A. J. Zermansky et al., *Towards global and long-term neurological gene therapy unexpected transgene dependent, high-level, and widespread distribution of HSV-1 thymidine kinase throughout the CNS, Mol. Ther.*, 4:490-498 (2001); T. D. Southgate et al., *Long-term transgene expression within the anterior pituitary gland in situ: impact on circulating hormone levels, cellular and antibody-mediated immune responses, Endocrinology*, 142:464-476 (2001)].

Example 9

Intrastriatal Delivery of RAds in the 6-OHDA Experimental Model of PD and Quantification of RAd-Mediated Protection of Dopaminergic Neurons in the Substantia Nigra Pars Compacta Adult male Fisher 344 rats of 200-250 grams body weight (obtained from Charles River Breeding Laboratories) were used. All animals had free access to food and water, a 12-hour light/dark cycle, and constant housing temperature and humidity, and experiments followed approved local regulations guiding experimental research. The ability of RAd-ShhN, RAd-Gli-1, or RAd-Nurr-1 to protect DA neurons from 6-OHDA neurotoxicity was evaluated using a modification of a robust experimental model of PD in rats [D. L. Choi-Lundberg et al., *Behavioral and cellular protection of rat dopaminergic neurons by an adenoviral vector encoding glial cell line-derived neurotrophic factor, Exp. Neurol.*, 154: 261-275 (1.998)]. Stereotaxic neurosurgery was performed on the animals under gaseous anesthetic as previously described [A. Hurtado-Lorenzo et al., *Adenovirus for gene transfer into the rat brain: evaluation of transfer efficiency, toxicity and inflammatory and immune reactions*, In: C. A. Machida, Editor, *Virus Vectors for Gene Therapy: Methods and Protocols*, Humana Press Inc., Totowa, N. J. (2003), 113-133], using the following stereotaxic coordinates from bregma: AP +1.0 mm, ML +3.2 mm, DV −5.0 mm for the right hemisphere injection and AP +1.0 mm, ML −3.2 mm, DV −5.0 mm for the left hemisphere injection. Using a 0.5-μl Hamilton syringe, a total volume of 0.02 μl of the retrograde tracer fluoro-gold (FG) (2% diluted in saline 0.9% w/v) was injected bilaterally, over a total of 6-7 minutes. The volume of FG was optimized to label a number of cells comparable to those labeled in the substantia nigra following the injection of RAds into the striatum. The following volumes of FG were tested: 0.2, 0.1, 0.05, and 0.02 μl of 2% FG. The tracer was injected into the striatum and the total number of retrogradely labeled striatal neurons was counted. The injection of 0.02 μl of 2% FG consistently labeled a range of 30-50 neurons per 25-μm-thick midbrain section throughout the nigra (a total mean of 1647 neurons for all sections throughout the substantia nigra); this number was comparable to the number of neurons retrogradely labeled following the injection of RAd. Therefore, this volume of FG was chosen for the experiments.

Following the FG injection, 3 μl of RAd (1×10$^8$ IU) was injected into the right hemisphere, using a 10-μl Hamilton syringe, at the identical coordinates used for the first injection of FG. One week later, the animals were prepared for a second surgery, during which 21 μl of 6-OHDA-HCl, resuspended in ascorbic acid 0.2 mg/ml and diluted in saline 0.9% w/v to a final concentration of 8 μg/μl, was injected over 6 minutes into the right striatum in exactly the same anatomical site previously injected with FG and RAd. Animals were sacrificed four weeks after injection of 6-OHDA and the brains fixed by cardiac perfusion with oxygenated tyrode followed by 4% paraformaldehyde, pH 7.4, as previously described in detail [C. E. Thomas et al., *Gene transfer into rat brain using adenoviral vectors*, In: J. N. Gerfen, R. McKay, M. A. Rogawski, D. R. Sibley and P. Skolnick, Editors, *Current Protocols in Neuroscience*, Wiley, New York (2000), 4.23.1-4.23.40; A. Hurtado-Lorenzo et al., *Adenovirus for gene transfer into the rat brain: evaluation of transfer efficiency, toxicity and inflammatory and immune reactions*, In: C. A. Machida, Editor, *Virus Vectors for Gene Therapy: Methods and Protocols*, Humana Press Inc., Totowa, N.J. (2003), 113-133]. Brains were post-fixed for 6 hours at 4° C., washed with PBS, and stored in PBS containing 0.1% sodium azide at 4° C. until required. Coronal sections (25 μm thickness) of the midbrain or the forebrain (40 μm) were cut using an electronic Vibratome (obtained from Leica). The midbrain was sectioned from AP −4.52 mm to AP −6.30 mm. The forebrain was sectioned from AP 3.20 mm to AP −1.30 mm according to the stereotactic rat brain atlas [G. Paxinos et al., *The Rat Brain in Stereotaxic Coordinates* (2nd ed.), Academic Press, San Diego (1986)].

The extent of neuroprotection was measured by counting, using the 20× objective, the number of FG-positive retrogradely marked nigrostriatal neurons throughout the rostrocaudal axis (AP −4.8 mm to AP −6.04) of the ipsilateral (lesioned) substantia nigra pars compacta (SNpc) and expressed as a percentage of the number of fluoro-gold-marked nigrostriatal neurons in the contralateral hemisphere (unlesioned); n=7 per group. The medial terminal nucleus of the accessory optic tract was used to define the border between the SNpc and the VTA. Rats injected with RAd-GDNF or RAd-35 (β-galactosidase) were used as positive and negative controls, respectively. All neurons present in all 25-μm sections cut throughout the extent of the substantia nigra were counted. Any counting method in which the dependent variable enters into the statistical calculations (e.g., in which the percentage of neuronal survival and the counts are performed by someone who does not know the experimental manipulation or potential outcomes) can be used instead of stereology—stereology is useful mainly for unbiased estimations of very large numbers of cells. The operator performing the neuronal counts was blind to the identity of the sections (i.e., from either any of the control or any of the experimental groups). The estimation of the percentage of protected susceptible neurons (PSN) was calculated using the following mathematical correction:

$$PSN = \frac{\tilde{X} \text{ \% protected cells} - \tilde{X} \text{ \% survivor cells (negative control)}}{100 - \tilde{X} \text{ \% survivor cells (negative control)}} \times 100.$$

Example 10

Quantification of the Cell Body Area of Dopamine Nigral Neurons within the SNpc

The size of ipsilateral (lesioned side) dopaminergic neurons in RAd-treated animals and controls was measured as square micrometers of cell body area and expressed as a percentage of the cell body area of dopaminergic neurons in the contralateral site (unlesioned side). One hundred dopaminergic neurons were randomly chosen at the level of the rostral SNpc and used to estimate the area of neuronal somata; seven animals per group were used. The experimenter selected the neurons and was blind to the treatment groups. Measurements were made with a Leica Quantimet Q600 Image Analysis System controlled by QWIN software (obtained from Leica Microsystems; Cambridge, UK) connected to a Leica RMDB microscope.

Example 11

Quantification of the Density of Striatal Dopaminergic, Th-Immunoreactive, Fibers The extent of striatal dopaminergic denervation produced by the injection of the neurotoxin 6-OHDA and the effect of the potentially therapeutic RAds was evaluated by measuring the density of TH-IR fibers in the striatum. Six representative forebrain sections corresponding to the coordinates (from bregma) AP 1.60, AP 1.20, AP 1.00, AP 0.70, AP 0.48, and AP 0.20 were used to measure the density of TH-IR in the entire ipsilateral striatum and expressed as a percentage of an equivalent area in the contralateral site (n=4). All measurements were made with a Leica Quantimet Q600 Image Analysis System controlled by QWIN software (obtained from Leica Microsystems) connected to a Leica RMDB microscope.

Example 12

Statistical Analysis

The treatment groups (RAd-ShhN, RAd-Gli-1, RAd-Nurr-1, RAd-35, RAd-GDNF) were compared by ANOVA or repeated-measures ANOVA with Tukey-Kramer (multiple comparisons test) or Dunnett post hoc pair-wise comparisons. Statistical calculations were made using the Graphpad Instat v2.00 statistical package.

Example 13

Molecular Characterization of Recombinant Adenoviral Vectors

The shuttle vectors encoding GDNF, ShhN, Gli-1, or Nurr-1 were co-transfected with the adenovirus 5 (Ad5) genomic plasmid pJM17 into 293 cells; the structure of the expected recombinant vectors is shown in FIG. 1a. After the onset of cytopathic effect (CPE), infected cells were collected and their DNA was extracted to characterize the recombinant adenoviruses and confirm the presence of the transgenes within the adenoviral genome (RAd-GDNF, FIGS. 1b and 1c; RAd-ShhN, FIGS. 1d and 1e; RAd-Gli-1, FIGS. 1f and 1g; the construction of RAd-Nurr-1 is not illustrated in detail).

FIG. 1b shows the restriction pattern and FIG. 1c the Southern blot hybridization of the shuttle vector pALGDNF (lane 1), RAd-GDNF (lane 2), the Ad5 genomic plasmid pJM17 (lane 3), and the molecular weight (MW) markers (lane 4). DNA was extracted and digested with HindIII to release the insert (0.7 kb) together with the major immediate early hCMV promoter (0.7 kb), resulting in the generation of a 1.4-kb fragment (FIGS. 1b and 1c) from the shuttle vector (lanes 1), and the RAd-GDNF (lanes 2), but not from pJM17 (lanes 3). Southern blot hybridization was used, utilizing a GDNF-specific 0.7-kb DIG-labeled probe corresponding to the full-length GDNF cDNA, to identify the 1.4-kb band. As shown in FIG. 1c the shuttle vector (lane 1) and RAd-GDNF (lane 2) exhibited the expected 1.4-kb positive hybridization signal, whereas this signal was absent from the plasmid pJM17 (lane 3).

A recombinant adenovirus encoding ShhN under the control of the hCMV promoter (RAd-ShhN) was also constructed. The viral DNA was extracted and digested with HindIII. FIG. 1d shows the restriction patterns of RAd-ShhN (lane 1) and the shuttle vector pALShhN (FIG. 1d, lane 2) used as positive control. The HindIII digestion resulted in the release of a 0.9-kb fragment that corresponds to the ShhN coding region together with the hCMV promoter (FIG. 1d, lanes 1 and 2). The identity of the 0.9-kb band was confirmed by Southern blot hybridization using a homologous DIG-labeled probe corresponding to the ShhN cDNA. As shown in FIG. 1e, the probe specifically hybridized with the 0.9-kb band of RAd-ShhN (FIG. 1e, lane 1) and the shuttle vector pALShhN (FIG. 1e, lane 2).

Following the co-transfection of the shuttle vector pAL-Gli-1 together with the Ad5 genomic plasmid PJM17 into 293 cells, and the onset of CPE, the viral DNA was extracted and digested with HindIII to confirm the presence of the Gli-1 transgene within the Ad5 genome. FIG. 1f shows the restriction pattern of RAd-Gli-1 in lane 1. The digestion released the insert (3.6 kb) together with the poly(A) signal (0.4 kb) that results in the generation of a 4.0-kb fragment. The shuttle plasmid pALGli-1 digested with HindIII was used as positive control for the presence of the expression cassette (FIG. 1f, lane 3), and the HindIII-digested Ad5 genomic plasmid pJM17 (FIG. 1f, lane 2) as negative control. To confirm the identity of the 4.0-kb band a Southern hybridization was performed, using as a probe the Gli-1 cDNA fragment labeled with DIG. A positive hybridization signal was detected in the lane corresponding to RAd-Gli-1 (FIG. 1g, lane 1) as well as in the lane corresponding to the shuttle vector pALGli-1 digested with HindIII (FIG. 1g, lane 3). In contrast, no hybridization signal was detected in the digested viral plasmid pJM17 (FIG. 1g, lane 2) used as negative control Example 14

Figure 2:
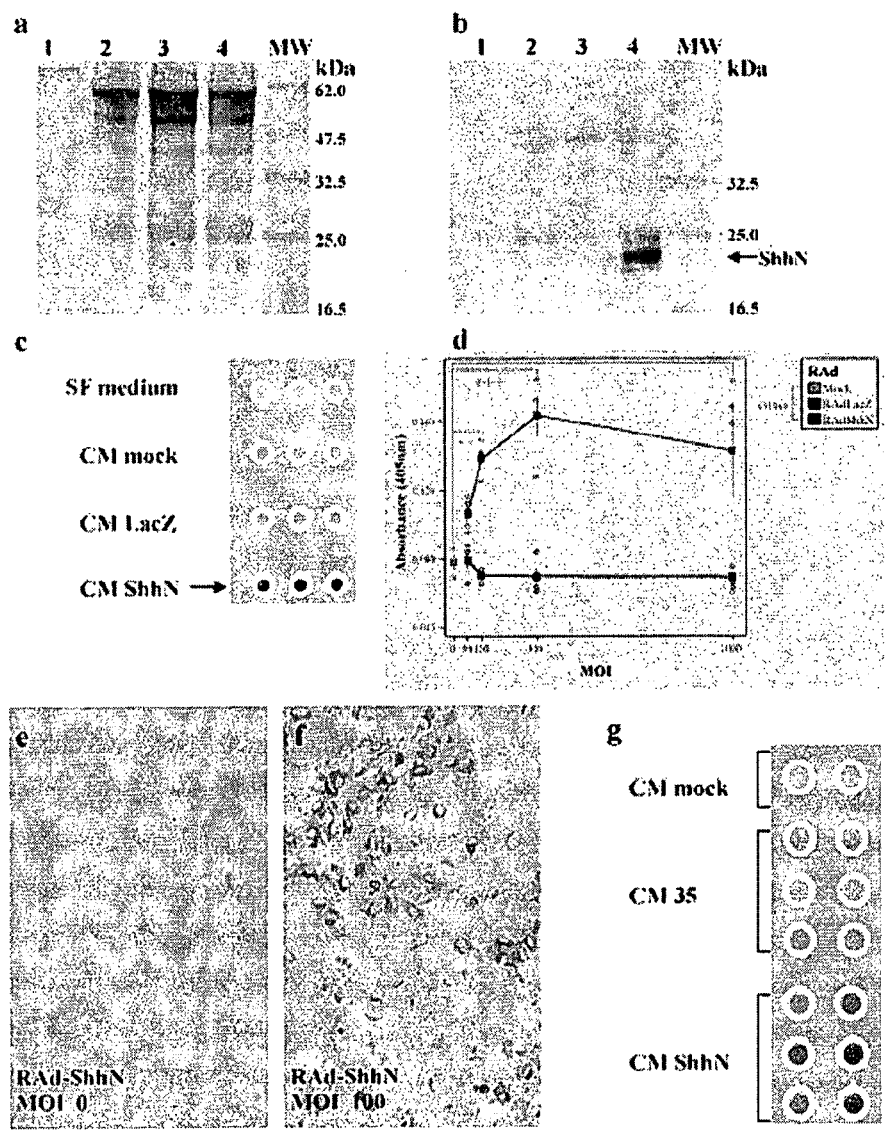
FIG. 2 illustrates that ShhN is produced and released by BHK or glial cells infected with RAd-ShhN in accordance with an embodiment of the present invention. The presence of ShhN in the supernatant of BHK cells infected with RAd-ShhN is shown in (a, b) a Western blot analysis, (c) a dot blot, and (d) an ELISA. Electrophoretic separation of conditioned medium (CM) from RAd-infected BHK cells on 10% Nu-PAGE gel is shown in (a). Lanes 1-4 contain 25-fold-concentrated samples from the different CM: (1) serum-free (SF) medium, (2) CM mock, (3) CM LacZ, (4) CM ShhN. MW corresponds to molecular weight standards. Western blot analysis (b) confirmed that ShhN (approx 20 kDa) was released into culture medium after RAd-ShhN infection. Dot-blot analysis is illustrated in (c): 200 μl of 50% conditioned medium from RAd-infected BHK cells was immunoreacted with anti-ShhN antibodies. This assay demonstrated that ShhN was detected only in the conditioned medium from BHK cells infected with RAd-ShhN. This assay was carried out using conditioned medium at the same concentration used for bioactivity assays. Conditioned medium from BHK cells infected with increasing m.o.i. of 0-1000, and assayed for ShhN using an ELISA, is shown in (d). Two way ANOVA: m.o.i. $F327=1.586$, $P \geq 0.05$. RAd $F127=72.423$, $P \leq 0.001$. RAd*m.o.i. $F327=3.231$, $P \leq 0.05$ (+). Dunnett t (two-tailed) post hoc test for RAd effects: RAd-CMV-ShhN vs mock, $P \leq 0.001$, but RAd-35 vs mock, $P \geq 0.05$. Dunnett t (two-tailed) post hoc test for RAd*m.o.i. interaction: RAd-ShhN 100 vs mock, $P \leq 0.05$ (++); RAd-ShhN 300 vs mock (+++); and RAd-ShhN 1000 vs mock, $P < 0.01$ (++). The other possible RAd*m.o.i. combinations were not significant compared to mock-infected cultures. This illustrates that the release of ShhN into the medium, following RAd-ShhN-infection of BHK cells, increased proportionally to RAd-ShhN m.o.i. and reached its peak at 300 m.o.i.; this m.o.i. was selected for production of the conditioned media for further bioactivity studies. In addition, to test whether ShhN would also be produced and released from rodent glial cells, primary cultures of glial cells were infected with RAd-ShhN. The control cells are illustrated in (e) and infected cells expressing ShhN are shown in (f). Release of ShhN into the supernatant, analysis by dot blot, is shown in (g). Two hundred microliters of 50% conditioned medium from mock or RAd-infected glial cells was immunoreacted with a specific anti-ShhN antibody. This assay demonstrated that ShhN was released only into the conditioned medium originating from glial cells infected with RAd-ShhN.

Release of ShhN by BHK or Primary Cultures of Glial Cells Infected with RAd-ShhN Previously, it was demonstrated that by expressing the ShhN-terminal sequence, it is possible to obtain a functional and soluble peptide [A. Lopez-Martinez et al., *Limb-patterning activity and restricted posterior localization of the amino-terminal product of Sonic hedgehog cleavage, Curr. Biol.,* 5:791-796 (1995); C. M. Fan et al., *Long-range sclerotome induction by sonic hedgehog: direct role of the amino-terminal cleavage product and modulation by the cyclic AMP signaling pathway, Cell,* 81:457-465 (1995); R. B. Pepinsky et al., *Identification of a palmitic acid-modified form of human Sonic hedgehog, J. Biol. Chem.,* 273:14037-14045 (1998); H. Roelink et al., *Floor plate and motor neuron induction by different concentrations of the amino-terminal cleavage product of sonic hedgehog autoproteolysis, Cell,* 81:445-455 (1995); X. Zeng et al., *A freely diffusible form of Sonic hedgehog mediates long-range signalling, Nature,* 411: 716-720 (2001)]. To evaluate whether RAd-ShhN expressed a soluble form of the ShhN peptide, BHK cells were infected with RAd-ShhN at m.o.i. 300 for 6 hours, after which the supernatant was replaced and the cells were incubated for a further 48 hours. After 48 hours, the supernatant was collected and the proteins were concentrated. BHK cells infected with a RAd expressing β-galactosidase (RAd-35), uninfected cells, or uninfected cells grown in the absence of serum were used as negative controls. The presence of ShhN in the supernatant was detected by Western blot (FIGS. 2a and 2b). A 20-kDa band corresponds to the predicted molecular weight of ShhN. This band was immunoreactive for the specific anti-Shh monoclonal antibody 5E1 in the sample obtained from RAd-ShhN-infected cells (FIG. 2b, lane 4). Such an immunoreactive band was not detected in the samples obtained from BHK cells infected with RAd-35 (FIG. 2b, lane 3), uninfected cells (FIG. 2b, lane 2), or uninfected cells cultured in the absence of serum (FIG. 2b, lane 1).

Dot-blot analysis also further confirmed that ShhN was secreted into the medium, whereas it was not detected in the media from RAd-35-infected cells, uninfected cells, or cells uninfected and cultured in the absence of serum (FIG. 2c). Finally semiquantitation of the levels of ShhN peptide released to the medium using an ELISA technique demonstrated a m.o.i.-dependent increase in secreted ShhN, reaching its peak at 300 m.o.i. (FIG. 2d).

In vivo, mostly glial cells will be infected by RAd. Thus, to determine if glial cells could produce ShhN and release it into the medium, primary cultures of glial cells were infected with increasing concentrations of RAd-ShhN and either immunostained for ShhN (FIGS. 2e and 2f) or evaluated the culture medium for its content of released ShhN (FIG. 2g). These data showed that glial cells do express ShhN and can release it into the medium, supporting the use of RAd-ShhN in in vivo applications.

Example 15

In Vitro Bioactivity of ShhN

Conditioned Media from Cultures Infected with RAd-ShhN Promote the Survival of Dopamine Neurons in Primary Cells In vivo ShhN would be expected to be released and then act on dopamine neurons to exert its effects. This model was tested first in culture. To determine whether the ShhN peptide encoded by RAd-Shh and released from infected cells would protect dopaminergic neurons in vitro, VM cultures were maintained in 50% CM from BHK cells infected with RAd-ShhN(CM-ShhN) or RAd-35 (CM-35) or uninfected. VM cultures were maintained under stringently serum-free conditions (i.e., at no time were the cells exposed to serum). Further, to assess the specificity of the effects of CM-ShhN on DA neuronal survival, conditioned medium from either mock or RAd-infected BHK cells was incubated with or without a monoclonal anti-Shh blocking antibody before adding it to the VM cultures. The cultures were kept in different CM with or without Shh-blocking antibody for three days and then processed for TH immunocytochemistry to determine the effects of the treatments on dopaminergic neuron survival.

Figure 3:
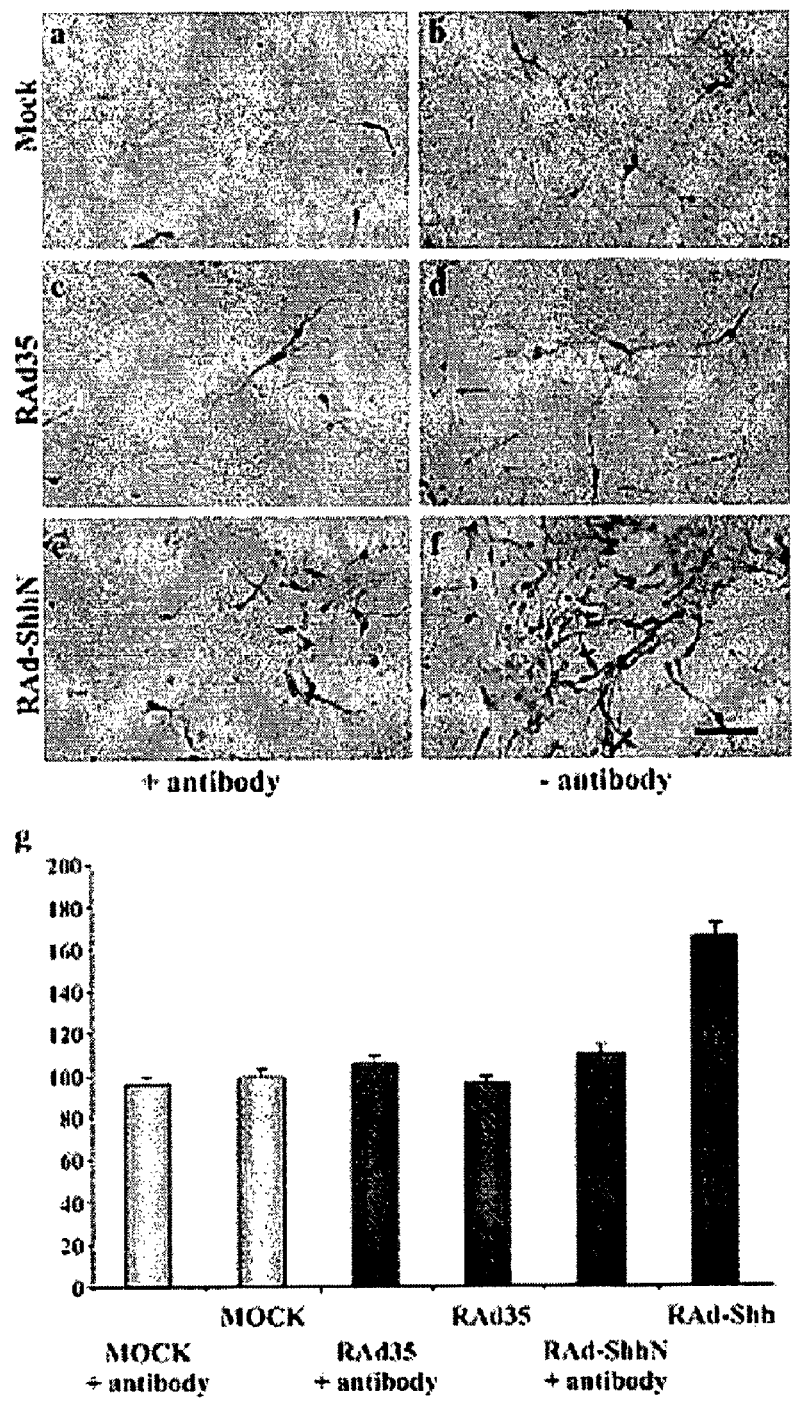
FIG. 3 illustrates that RAd-ShhN increases the survival of dopaminergic neurons (TH+ neurons) in ventral-mesencephalic (VM) cultures, in accordance with an embodiment of the present invention. E14 VM cultures were incubated for four days with (a, b) CM from mock-infected BHK cells or CM from BHK cells infected with (c, d) RAd-35 or (e, f) RAd-ShhN. In parallel cultures cells were pretreated with the anti-ShhN blocking antibody 5E1 (the effects of anti-Shh Ab are not illustrated; a, c, e). Anti-ShhN antibody was co-administered to the different conditioned media to a final dilution of 1:500. Neuron numbers were assessed and are expressed as the percentage of TH+ neurons per well, relative to mock-infected treatment in the absence of anti-ShhN antibody (means±SEM); this is illustrated in (g). Compared with the other treatments, CM ShhN significantly increased the number of TH+ neurons in the absence but not in the presence of anti-Shh antibody (g). CM-mock+antibody (n=12), 86.68±6.47; CM-mock (n=12), 100.00±6.73; CM-RAd-35+ antibody (n=12), 103.62±9.84; CM-RAd-35 (n=12), 97.46±4.12; CM-Shh+antibody (n=12), 112±8.22; CM-Shh (n=12), 159.82±9.51. Two way ANOVA followed by Tukey post hoc analysis indicated that the group treated with RAd-ShhN was statistically significantly different (P≦0.001) from all other groups, and there was no statistically significant difference between any of the other treatments. This experiment was repeated at least three times. a-f and g originate from different experiments. Images were chosen to illustrate neuronal morphology; quantitation was chosen to determine the statistical significance of the results.

FIG. 3 illustrates the response of VM-TH+ neurons to the different treatments. FIGS. 3a-3f illustrate that the survival of TH+-immunoreactive neurons in culture is increased only in cultures treated with CM from RAd-ShhN-infected cells (FIG. 3f) and that this increase is blocked by pretreatment of the CM with anti-ShhN antibodies (FIG. 3e). Further, FIG. 3 shows that control CM maintained a lower number of TH+-immunoreactive neurons in culture and that this effect could not be inhibited by anti-ShhN antibodies.

The quantification of these experiments is shown in FIG. 3g. CM from cells infected with RAd-ShhN enhanced dopaminergic neuron survival by approx 160%, and preincubation with anti-ShhN antibodies resulted in the complete inhibition of such trophic effects. This demonstrates that the increase in DA neuronal survival in CM removed from BHK cells infected with RAd-ShhN is due to the presence of ShhN in the CM. In the absence of ShhN-blocking antibodies, only the CM from BHK infected with RAd-ShhN significantly improved survival of TH+ neurons in VM cultures. In contrast, in the presence of ShhN-blocking antibodies, all CM provided comparable levels of TH+ neuronal survival, indicating that the levels of uncharacterized BHK-derived trophic factors were similar in all CM and that these uncharacterized activities did not include ShhN.

Example 16

In Vitro Bioactivity of ShhN and Gli-1

Figure 4:
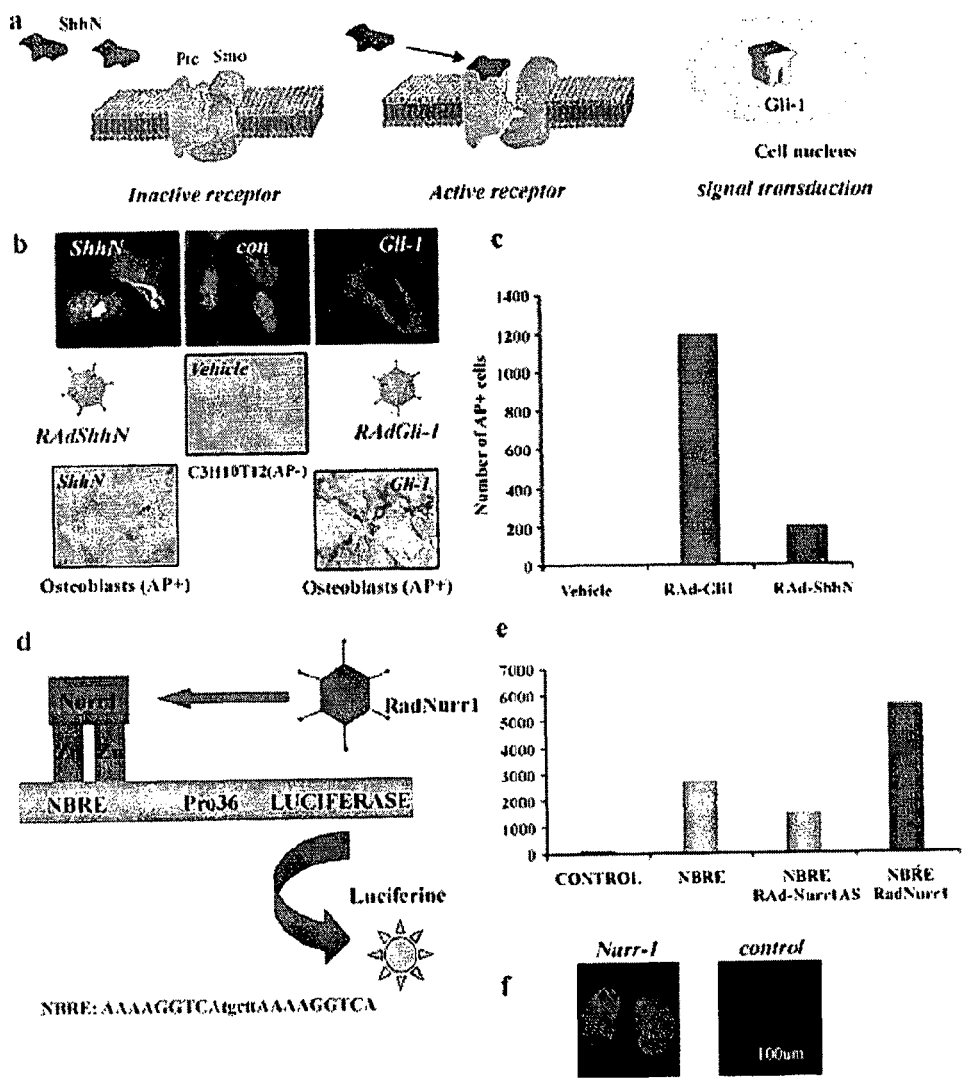
FIG. 4 illustrates the bioreactivity of RAd-ShhN in accordance with an embodiment of the present invention. (a) In vitro bioactivity of RAd-ShhN, RAd-Gli-1, and RAd-Nurr-1. A schematic view of the mechanism of action of ShhN, and Gli-1, is shown. This illustrates the interaction of ShhN with Ptc and Smo, the release of the inhibition on Smo, and the eventual stimulation of activated Gli-1 translocation into the nucleus to activate further downstream target genes. (b) The bioactivity of RAd-ShhN and RAd-Gli-1. HeLa cells were infected with RAd-ShhN, or RAd-Gli-1, or a negative control vector, at m.o.i. 200 IU/cell, and 48 hours later cells were fixed and the proteins detected with specific primary antibodies and immunofluorescently labeled secondary antibodies. Most of the ShhN immunoreactivity highlighted the Golgi apparatus, compatible with the intracellular distribution of a secretory protein, while Gli-1 showed both a cytoplasmic and a nuclear localization, as expected from a transcription factor that has been shown to shuttle between the cytoplasm and the nucleus. Differentiation of the pluripotential cell line C3H10T1/2 into osteoblasts was induced upon infection with RAd-ShhN, or RAd-Gli-1, following infection at m.o.i. 200. Alkaline phosphatase (AP) activity was used as a marker for osteoblast differentiation. Both vectors induced AP activity, and the quantitative analysis of AP+ cells is illustrated in (c). (d, e) The transcriptional activation mediated by RAd-Nurr-1 is shown. COS-7 cells were transfected with the reporter plasmid NBRE-Luciferase (d), containing the binding site for Nurr-1, and infected with RAd-Nurr-1 in sense orientation or RAd-Nurr-1 in antisense orientation (RAd-Nurr-1AS), used as negative control. (e) Luciferase activity was measured 48 hours after. The transcription factor Nurr1 binds to the canonical NBRE domain and induces expression of luciferase. (f) COS-7 cells were infected with RAd-Nurr-1, or a negative control vector, at m.o.i. 200 IU/cell, and 48 hours later cells were fixed and immunostained with antibodies recognizing Nurr1.

Infection of the Pluripotent Cell Line C3H10T1/2 with RAd-ShhN or RAd-Gli-1 Induces Osteoblastic Differentiation Biochemical and genetic data suggest that the receptor for Shh is the product of the tumor suppressor gene patched (ptc) [J. Motoyama et al., Ptch2, a second mouse Patched gene is co-expressed with Sonic hedgehog, Nat. Genet., 18:104-106 (1998); V. Marigo et al., Biochemical evidence that patched is the Hedgehog receptor, Nature, 384:76-179 (1996)]. The Shh signal is received and transduced at the membrane via a receptor complex consisting of ptc and smo. Ptc is a 1500-amino-acid glycoprotein with 12 membrane-spanning domains [Y. Nakano et al., A protein with several possible membrane-spanning domains encoded by the Drosophila segment polarity gene patched, Nature, 341:508-513 (1989)] and two extracellular loops that are required for Shh binding [V. Marigo et al., Biochemical evidence that patched is the Hedgehog receptor, Nature, 384:76-179 (1996); D. M. Stone et al., The tumour-suppressor gene patched encodes a candidate receptor for Sonic hedgehog, Nature, 384:129-134 (1996)]. Smo is a 115-kDa protein [J. Alcedo et al., The Drosophila smoothened gene encodes a seven-pass membrane protein, a putative receptor for the hedgehog signal, Cell, 86:221-232 (1996)]. In the absence of Shh, Smo and Ptc form an inactive complex. When Shh binds to Ptc, the complex is altered and Smo is released from inhibitory control to transduce an activating signal to the nucleus [D. Kalderon, Transducing the hedgehog signal, Cell, 103:371-374 (2000)] (FIG. 4a); this activates Gli-1, a transcription factor proposed to be a major mediator of the Shh signal [C. C. Hui et al., Expression of three mouse homologs of the Drosophila segment polarity gene cubitus interruptus, Gli, Gli-2, and Gli-3, in ectoderm-and mesoderm-derived tissues suggests multiple roles during postimplantation development, Dev. Biol., 162: 402-413 (1994); J. Lee et al., Gli1 is a target of Sonic hedgehog that induces ventral neural tube development, Development, 124:2537-2552 (1997); K. A. Platt et al., Expression of the mouse Gli and Ptc genes is adjacent to embryonic sources of hedgehog signals suggesting a conservation of pathways between flies and mice, Mech. Dev., 62:121-135 (1997); H. Sasaki et al., A binding site for Gli proteins is essential for HNF-3beta floor plate enhancer activity in transgenics and can respond to Shh in vitro, Development, 124:1313-1322 (1997)] (FIG. 4a). Previous studies [N. Kinto et al., Fibroblasts expressing Sonic hedgehog induce osteoblast differentiation and ectopic bone formation, FEBS Lett., 404:319-323 (1997)] demonstrated that conditioned medium containing ShhN was able to induce differentiation of the pluripotential fibroblast-like cell line C3H10T1/2 into osteoblasts, as determined by the induction of AP activity, an early marker of bone differentiation. Based on these observations an experiment was designed to test whether RAd-Gli-1 could replicate the morphogenetic properties of Shh. In this experiment 50% confluent C3H10T1/2 cells were mock infected with PBS or with RAd-Gli-1 at an m.o.i. 200. AP activity was detected eight days after infection using the Fast Red Kit (obtained from Sigma). C3H10T1/2 cells infected with RAd-ShhN at m.o.i. 200 were used as a positive control. As shown in FIGS. 4b and 4c, infection with RAd-Gli-1 and RAd-ShhN was able to induce differentiation of the pluripotent cell line C3H10T1/2 into osteoblasts as inferred from the detection of AP activity. As expected from a protein targeted to the secretory pathway, ShhN immunoreactivity outlined the ER/Golgi compartments (FIG. 4b). Gli-1 has been shown to shuttle between the cytoplasm and the nucleus. Thus, the immunoreactivity detected in both the cytoplasm and the nucleus is expected from previous knowledge of the subcellular distribution and function of Gli-1 (FIG. 4b; note that due to the different levels of expression in either compartment the figure shows higher cytoplasmic localization). In contrast, cells incubated with PBS did not induce osteoblast differentiation of this cell line. These results demonstrated that RAd-Gli-1 encodes a transcription factor that is biologically active, and, more importantly, that it is able to mimic the effects of ShhN in vitro.

Example 17

In Vitro Bioactivity of RAd-Nurr-1

The bioactivity of RAd-Nurr-1 was tested using COS-7 cells transiently transfected with a reporter plasmid containing the Nurr-1-responsive element NBRE upstream of the prolactin promoter (Pro36), as illustrated in FIG. 4d. Expressed Nurr-1 binds to the NBRE and stimulates Pro36-driven luciferase expression. Infection of transfected COS-7 cells with RAd-Nurr-1 increased luciferase expression two to three times over control values. Uninfected cells, or cells infected with a vector expressing the antisense noncoding strand of Nurr-1, did not induce luciferase expression over the basal activity of the reporter construct even in the absence of infection with RAd-Nurr-1 (FIG. 4e). Immunohistochemistry of control COS-7 cells infected with RAd-Nurr-1 indicates strong immunoreaction for Nurr-1 in the nucleus of infected cells (FIG. 4f).

Example 18

Figure 5:
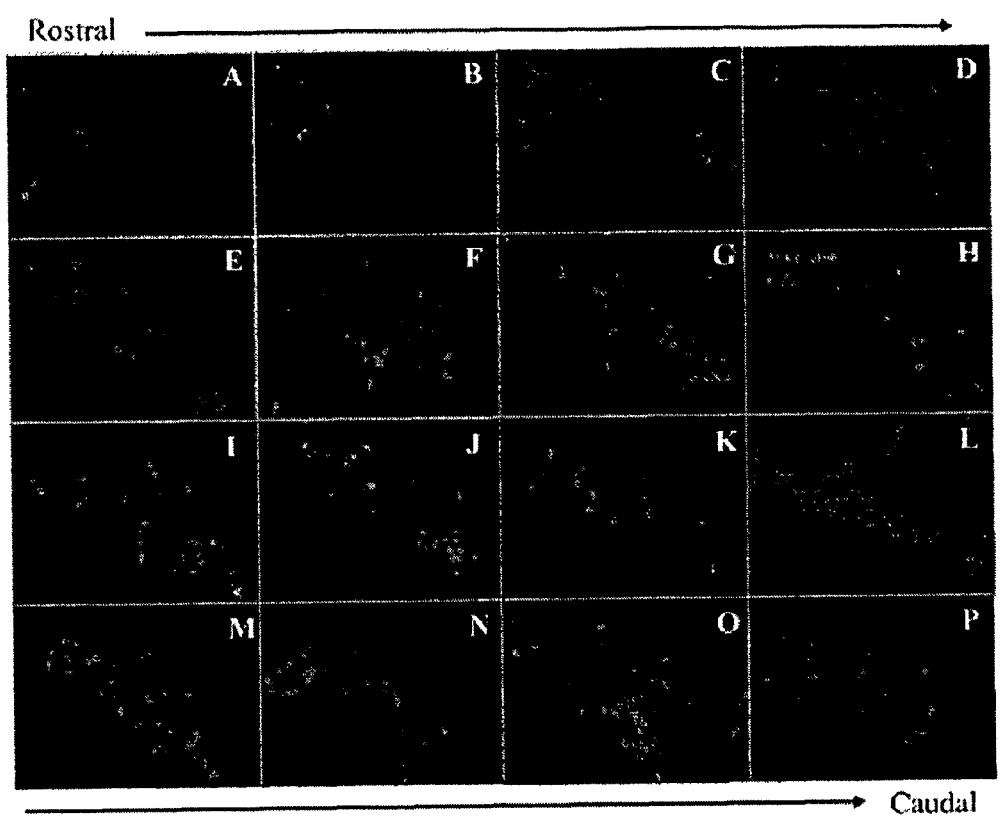
FIG. 5 illustrates retrograde targeting of nigrostriatal dopaminergic neurons throughout the rostrocaudal extent of the substantia nigra in accordance with an embodiment of the present invention. A recombinant adenovirus encoding the reporter gene thymidine kinase (RAd-TK, $3.2 \times 10^7$ IU) was stereotaxically injected into the rat dorsal striatum (AP +1.0 mm, ML +3.2, DV −5.0 mm). Retrograde transport of this vector to the substantia nigra pars compacta (SNpc) was verified one week after the injection, by immunostaining of TK protein using specific anti-HSV TK antibodies. (A-P) The expression of TK throughout the rostrocaudal axis of the SNpc from (A) AP-4.8 to (P) AP-6.30.

Distribution of Transgenes Throughout the Rostrocaudal Extent of the Substantia Nigra Following the Injection of RAds into the Striatum To determine the distribution throughout the rostrocaudal extent of the substantia nigra of an intracellular transgene expressed from an RAd, RAd-TK was injected into the striatum and the immunocytochemical distribution of the transgene was assessed in retrogradely labeled neurons in the substantia nigra. RAd-TK encodes the full-length herpes simplex virus type 1 thymidine kinase, HSV-1 TK [R. A. Dewey et al., *Chronic brain inflammation and persistent herpes simplex virus 1 thymidine kinase expression in survivors of syngeneic glioma treated by adenovirus-mediated gene therapy: implications for clinical trials*, Nat. Med., 5:1256-1263 (1999); A. J. Zermansky et al., *Towards global and long-term neurological gene therapy: unexpected transgene dependent, high-level, and widespread distribution of HSV-1 thymidine kinase throughout the CNS*, Mol. Ther., 4:490-498 (200.1)]. The wide distribution throughout the rostrocaudal extent of the transgene TK detected immunocytochemically throughout the substantia nigra is illustrated in FIG. 5.

Example 19

Figure 6:
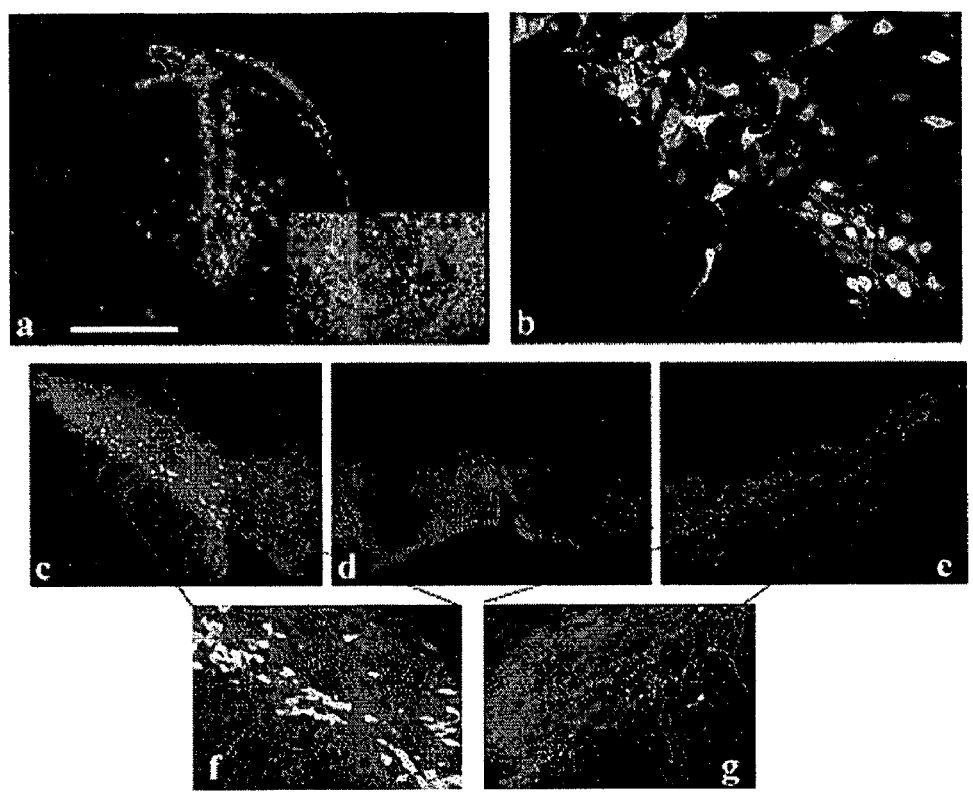
FIG. 6 illustrates a method for combined retrograde targeting of substantia nigra dopaminergic neurons with both fluoro-gold and adenoviral vectors in accordance with an embodiment of the present invention. The method used to retrograde target RAd and fluoro-gold to anatomically overlapping areas in the substantia nigra is illustrated. The method was exhaustively optimized to label a comparable amount of nigrostriatal neurons (range 30-50) by each method. Also illustrated is the degeneration of fluoro-gold+ cells after administration of 6-OHDA and the fact that all neurons retrogradely labeled with fluoro-gold indeed are TH-positive. All neurons retrogradely labeled by RAd were also TH-positive (not illustrated). (a) A coronal section through the striatum showing colocalization of the fluorescent tracer fluoro-gold (green) and RAd-expressed transgene (red), following their stereotaxic injection into the rat brain at the level of the dorsal striatum, using coordinates identical to those used for the neurotoxicity experiments (scale bar, 1 mm). For these experiments RAd-TK (encoding an intracellular gene product) was injected into the striatum, as described for FIG. 5. One week later, the progressive degeneration of the nigrostriatal pathway was induced by injection of 6-OHDA at the same coordinates used for fluoro-gold and RAd. (b) A coronal section of the substantia nigra. Fluoro-gold has been retrogradely transported to the substantia nigra (green), and RAd-expressed transgene is detected by immunocytochemistry (red). Double labeling demonstrates colocalization (yellow) of fluoro-gold (green) and RAd-encoded TK (red) in the neurons of the SNpc. Expression of the encoded marker transgene was detected by indirect immunofluorescence. Sections illustrated in (c-g) show coronal sections of the substantia nigra immunoreacted for TH and evaluated for the presence of fluoro-gold. Dopaminergic neurons were detected by immunofluorescence using a specific anti-TH antibody. Notice the degeneration of fluoro-gold+ neurons after intrastriatal injection of 16 μg of 6-OHDA (e.g., e, low-power view of the substantia nigra; g, high-magnification view). In the contralateral side, vehicle (saline) injection in the striatum does not induce degeneration (c and f, c, low-power view of the substantia nigra; f, high-magnification view). Colocalization (yellow) indicates that every fluoro-gold+ neuron (green) is TH+ (red).

Combined Retrograde Targeting of Substantia Nigra Dopaminergic Neurons with Both Fluoro-Gold and Adenoviral Vectors FIG. 6 illustrates the injection site and distribution of fluoro-gold (green) in the striatum, as well as the site of injection of RAd, detected by immunocytochemistry for the transgene (red) (FIG. 6a). The overlap between both labels indicates that fluoro-gold and RAd have distributed over an equivalent area of striatal tissue. FIG. 6b shows the detection of retrogradely transported fluoro-gold in neurons also expressing a RAd-encoded transgene. This demonstrates that RAd-encoded therapeutic transgene expression occurs in nigral neurons that project to the striatum. Finally, FIGS. 6c-6g indicate that all neurons containing the retrogradely transported dye fluoro-gold are TH+ nigral neurons and thus identifies these as bona fide dopaminergic nigrostriatal neurons.

Example 20

RAd-ShhN and RAd-Gli-1, but not RAd-Nurr-1 Protect Dopaminergic (DA) Nigrostriatal Neurons Against 6-OHDA-Induced Neurodegeneration In Vivo The ability of RAd-Shh and RAd-Gli-1 to protect DA neurons from 6-OHDA neurotoxicity was evaluated using a modification of the rat model of PD reported by Choi-Lundberg [D. L. Choi-Lundberg et al., *Behavioral and cellular protection of rat dopaminergic neurons by an adenoviral vector encoding glial cell line-derived neurotrophic factor*, Exp. Neurol., 154:261-275 (1998)] (illustrated in FIG. 6). Fluoro-gold was injected intrastriatally on both sides of the brain; during the same surgical intervention $1 \times 10^8$ IU of RAd-ShhN, RAd-Gli-1, RAd-Nurr-1, the negative control vector RAd-35, or the positive control RAd-GDNF was injected into the right striatum. One week later, retrograde degeneration of the nigrostriatal pathway was induced by unilateral (right dorsal striatum) administration of 16 μg of 6-OHDA-HCl using the same coordinates used for the delivery of fluoro-gold and RAd (referred to as the "ipsilateral site", and four weeks later, the rats were injected with an overdose of anesthetic, were perfused-fixed through the left ventricle of the heart, were postfixed overnight, and 25-μm-thick sections were cut on a vibratome and analyzed using an Olympus AHBS fluorescence photomicroscope. The surviving neurons were counted on the ipsilateral side (exposed to the neurotoxin) and expressed as a percentage of neurons of the contralateral (control) hemisphere.

Figure 7:
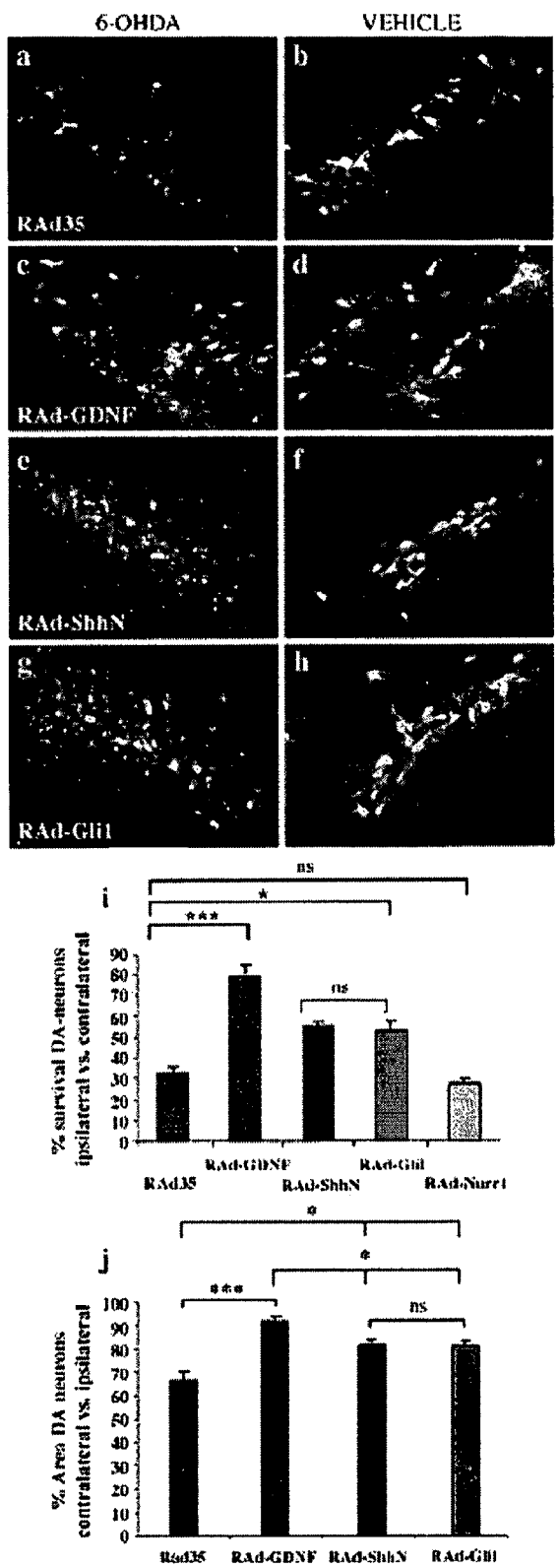
FIG. 7 illustrates effects of gene transfer on substantia nigra dopaminergic neurons in accordance with an embodiment of the present invention. Adenovirus-mediated gene transfer of $1 \times 10^8$ IU of (a, b) RAd-35, (c, d) RAd-GDNF, (e, f) RAd-ShhN, (g, h) RAd-Gli-1, or RAd-Nurr-1 (not illustrated) was tested against 6-OHDA-induced neurodegeneration of nigrostriatal cells retrogradely labeled with fluoro-gold. The side injected with 6-OHDA is shown on the left, and the control side is shown on the right. Injection of RAd-GDNF, RAd-ShhN, and RAd-Gli-1 protected a significant amount of nigrostriatal neurons compared to animals injected with the negative control vector RAd-35. Note the survival of large fluoro-gold+ neurons in the ipsilateral site of animals injected with RAd-ShhN (e), RAd-Gli-1 (g), and RAd-GDNF (c) compared with RAd-35 (a). The quantitative analysis is shown in (i) and also indicates the analysis of the animals injected with RAd-Nurr-1. Survival of nigrostriatal neurons was expressed as a percentage of unlesioned contralateral neurons. (0) The area occupied by dopamine neurons' cell bodies protected from degeneration after treatment with $1 \times 10^8$ IU of RAd-ShhN, RAd-Gli-1, or RAd-GDNF was quantified and expressed as a percentage of the neuron soma area in the contralateral site. RAd-GDNF, RAd-ShhN, and RAd-Gli-1 all protected cell body size compared with RAd-35. RAd-GDNF showed the strongest effect. Cell body protection by ShhN and Gli-1 was statistically significantly different from that of animals injected with RAd-35. The treatment groups were compared by repeated-measures ANOVA with post hoc Tukey or Dunnet multiple comparison test; *P≦0.05; ***P≦0.005.

Animals injected with the negative control vector RAd-35 preserved only 33.4±1.83% of nigrostriatal neurons (FIGS. 7a, 7b, and 7i). Neuronal counts indicated that throughout the SNpc of rats injected with RAd-ShhN, 53.3±1.29% of dopaminergic neurons survived on the lesioned site in comparison with the intact contralateral site (FIGS. 7e, 7f, and 7i). In animals injected with RAd-Gli-1 52.9±3.31% of fluoro-gold-labeled neurons survived (FIGS. 7g, 7h, and 7i), while 79±3.7% of retrogradely labeled dopaminergic neurons were protected from neurodegeneration by RAd-GDNF (FIGS. 7c, 7d, and 7i). Animals injected with RAd-Nurr-1 retained only 27±1.22% of labeled striatonigral neurons, a number not statistically different from that of animals injected with the negative control vector RAd-35 (FIG. 7i). These results demonstrate that intrastriatal delivery of $1 \times 10^8$ IU of RAd-ShhN and RAd-Gli-1 can protect a statistically significant proportion of nigrostriatal neurons susceptible to being killed by 6-OHDA [analysis of variance (ANOVA), F=38.33, P≦0.01, n=7]; RAd-GDNF protected a higher proportion of nigrostriatal neurons (ANOVA, F=38.33, P≦0.001, n=7), while RAd-Nurr-1, however, was ineffective.

Example 21

Figure 8:
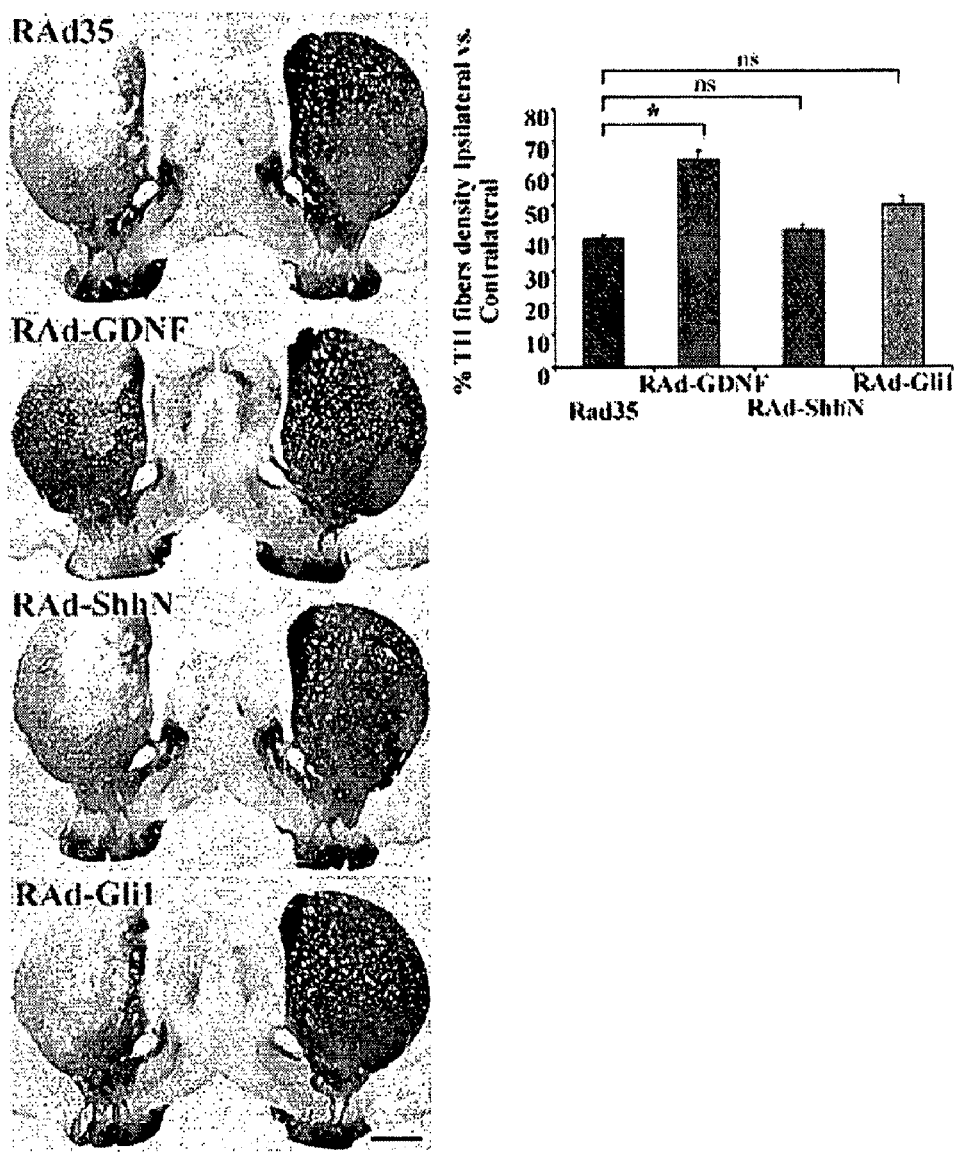
FIG. 8 illustrates effects of gene transfer on striatal dopaminergic innervation in accordance with an embodiment of the present invention. The column on the left illustrates sections throughout the striatum of treated animals immunoreacted with an antibody raised against TH, to reveal the density of TH-immunopositive fibers in the striatum. The lesioned side is on the left, the control side is on the right. Notice that only animals injected with RAd-GDNF showed a protection of the striatal dopaminergic fibers. The graph shows the densitometric analysis of TH+ fiber density in the striatum of rats treated with $1\times10^8$ IU of RAd-Shh, RAd-Gli-1, RAd-GDNF, or RAd-35. Degeneration of axonal terminals in the striatum after administration of 6-OHDA is not prevented following the injection of RAd-ShhN, RAd-Gli-1, or RAd-Nurr-1 (not shown). Only RAd-GDNF is able to protect TH+ fibers significantly. The treatment groups were compared by repeated-measures ANOVA with post hoc Tukey or Dunnet multiple comparison test; *$P \leq 0.05$. Scale bar, 1 mm.

RAd-ShhN or RAd-Gli-1 does not Protect Dopamine Neurons' Tyrosine-Hydroxylase-Immunoreactive Terminals in the Striatum: a Comparison with RAd-GDNF Having demonstrated that a single injection of $1\times10^8$ IU of RAd-Shh and RAd-Gli-1 is neuroprotective for retrogradely labeled dopaminergic neurons in the SNpc, it was examined whether these vectors could prevent 6-OHDA-induced dopaminergic denervation of the striatum. Forebrain coronal sections were processed from animals injected with $1\times10^8$ of RAd-ShhN or RAd-Gli-1 by immunohistochemistry to detect TH-immunoreactive (TH-IR) fibers in the striatum. The extent of striatal denervation produced by 6-OHDA was evaluated by measuring the density of TH-IR fibers in the entire ipsilateral striatum; this was expressed as a percentage of the contralateral site. The density of TH-IR fibers in the striatum of rats treated with RAd-ShhN and RAd-Gli-1 decreased to 42.4±1.26 and 50.62±4.25 of the contralateral site, respectively (FIG. 8). In rats treated with RAd-35, the density of TH-IR fibers decreased to 40±0.25% of controls, while in rats treated with RAd-GDNF, they decreased only to 64%±6.72 of control values (FIG. 8).

Statistical analysis of these data indicated that neither RAd-Shh nor RAd-Gli-1 was able to protect striatal axonal DA terminals from degeneration four weeks after injection of 6-OHDA (ANOVA, F=25.22, P≧0.05, n=4). Only the injection of RAd-GDNF resulted in a statistically significant increase (ANOVA, F=25.22, P≦0.01, n=4) in the density of TH-IR in comparison with RAd-35-treated rats. These results indicate that while RAd-mediated gene transfer of ShhN and Gli-1 results in the protection of DA neurons from 6-OHDA neurotoxicity, denervation of striatal DA terminals is not prevented.

Example 22

RAd-ShhN or RAd-Gli-1 Partially Protects Dopamine Striatonigral Neuronal Cell Bodies from Atrophy Induced by Intrastiatal Injection of the Neurotoxin 6-OHDA Although not wishing to be bound by any particular theory, the inventors hypothesized that if GDNF could protect the striatal dopaminergic innervation, it could also possibly protect the decrease in cell body size of dopaminergic neurons in the substantia nigra that is caused by dopaminergic denervation, with cells with larger terminal fields displaying larger sizes and vice versa. To test this hypothesis, the inventors measured the area occupied by nigrostriatal cell bodies (n=100 TH+ neurons on both the control and the neuroprotected substantia nigra) and expressed values of ipsilateral DA neuronal cell body area (neuroprotected) as a percentage of the cell body area of neurons in the contralateral substantia nigra (FIG. 7j). In rats injected with RAd-GDNF, cell body size decreased to 92±1.26% of the contralateral site. In contrast, in RAd-ShhN- and RAd-Gli-1-treated rats the cell body area of nigrostriatal neurons was reduced to 82% of the contralateral side neurons. Soma size in rats injected with the control vector RAd-35 decreased to 67±5.24% of the contralateral side. The reduction in size of dopaminergic neurons in rats treated with RAd-ShhN and RAd-Gli-1 was statistically significant (F=51.49, P≦0.01, n=100 dopaminergic neurons analyzed in total or F=14.054, P≦0.05, n=7 when the data are analyzed per number of animals studied) compared with the size of those in animals injected with RAd-GDNF. The reduction in cell body size in animals injected with the control vector RAd-35 was statistically significant compared with RAd-ShhN-, RAd-Gli-1-(ANOVA, F=51.49, P≦0.01, n=100 or F=14.054, P≦0.05, n=7), and RAd-GDNF-treated rats (ANOVA, F=51.49, P≦0.001, n=100 or F=14.054, P≦0.001, n=7).

These results indicate that, despite comparable striatal denervation seen in animals injected with 6-OHDA and treated with either RAd-ShhN and RAd-Gli-1 or the control vector RAd-35, only RAd-ShhN and RAd-Gli-1 treatment partially prevented the progressive decrease of nigrostriatal cell body size induced by the neurotoxin. This indicates that ShhN and Gli-1 can protect the size of dopamine neurons in the substantia nigra, independent from trophic effects at the level of the striatum and/or the striatal axonal terminals.

Example 23

Figure 9:
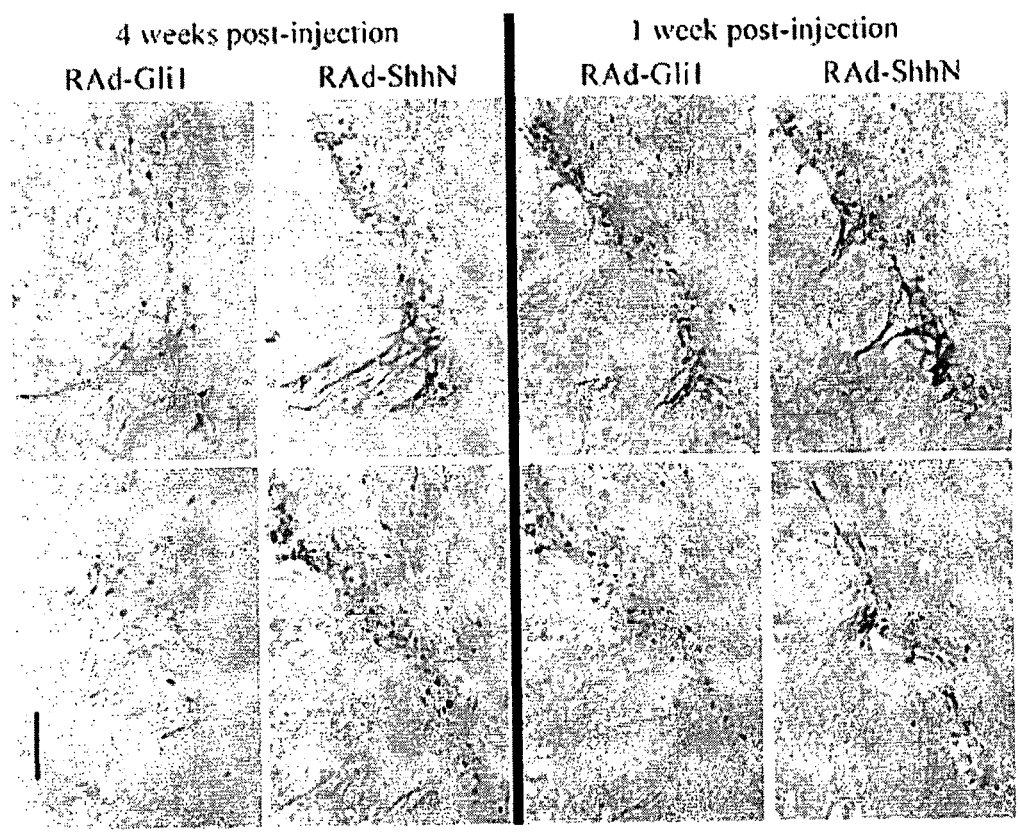
FIG. 9 illustrates transgene expression in the substantia nigra in accordance with an embodiment of the present invention. RAd-ShhN or RAd-Gli-1 was injected into the striatum and 1 or 4 weeks later animals were perfusion-fixed and brains were sectioned and probed with specific antibodies for either ShhN or Gli-1. Two rostrocaudal levels are shown for each condition. There was no specific immunostaining in either the contralateral substantia nigra or the uninjected animals. Scale bar, 200 µm.

Expression of ShhN and Gli-1 in the Substantia Nigra at 1 and 4 Weeks Following Their Injection into the Dorsal Striatum To confirm that the transgenes were present throughout the substantia nigra during the experimental procedure, the expression of ShhN and Gli-1 was determined in the substantia nigra at one and four weeks after their intrastriatal injection. Using specific immunohistochemical techniques, both transgenes could be detected in the substantia nigra at one or four weeks after the injection of viruses into the striatum (FIG. 9). This indicates that the potential neurotrophic factors were available in the substantia nigra at the proper time to exert their pharmacological effects. There was no positive immunoreaction in the contralateral substantia nigra (not shown). Immunoreactivity for Nurr-1 was present, but it was also present in many other areas of the rat brain, including the contralateral substantia nigra (not shown). Thus, due to the high levels of basal expression of Nurr-1 an increase due to RAd-Nurr-1 expression could not be detected.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method for treating Parkinson's disease in a mammal, comprising:
   providing a quantity of a viral vector expressing Gli-1; and
   administering a therapeutically effective amount of the quantity of viral vector to the mammal.

2. The method of claim 1, wherein the viral vector is selected from the group consisting of recombinant adenoviral vectors, recombinant adeno-associated viral vectors; herpes simplex virus type 1 vectors, and lentiviral vectors.

3. The method of claim 1, wherein the viral vector is a recombinant adenoviral vector.

4. The method of claim 1, wherein the quantity of viral vector expressing Gli-1 further comprises a quantity of viral vector expressing N-terminal of sonic hedgehog (ShhN).

5. The method of claim 1, wherein the quantity of viral vector expressing Gli-1 further expresses ShhN peptide.

6. The method of claim 1, wherein the quantity of viral vector expressing Gli-1 further expresses one or more dopaminergic neuron differentiation factors.

7. The method of claim 1, wherein the quantity of viral vector expressing Gli-1 further expresses sonic hedgehog (Shh) peptide.

8. The method of claim 1, wherein administering the therapeutically effective amount of the quantity of viral vector to the mammal results in protection of dopaminergic nigrostriatal neuronal cell bodies.

9. The method of claim 1, wherein the mammal is a human.

10. The method of claim 1, wherein the mammal is a rodent.

11. The method of claim 1, wherein the quantity of viral vector is administered to the mammal via direct injection.

12. The method of claim 1, wherein administering the therapeutically effective amount of the quantity of viral vector to the mammal results in protection against neurodegeneration and/or neurotoxicity.

* * * * *

UNITED STATES PATENT AND TRADEMARK OFFICE
CERTIFICATE OF CORRECTION

| | | |
|---|---|---|
| PATENT NO. | : 7,858,590 B2 | Page 1 of 1 |
| APPLICATION NO. | : 11/572397 | |
| DATED | : December 28, 2010 | |
| INVENTOR(S) | : Pedro Lowenstein and Maria Castro | |

It is certified that error appears in the above-identified patent and that said Letters Patent is hereby corrected as shown below:

In column 1, under the "Related Applications" section but before the "Field of the Invention" section, please insert the following:

--FEDERAL SUPPORT
The U.S. Government has a paid-up license in this invention and the right in limited circumstances to require the patent owner to license others on reasonable terms as provided for by the terms of Grant Nos. R01NS42893 and R01NS44556 awarded by the National Institutes of Health.--

Signed and Sealed this
Second Day of August, 2011

David J. Kappos
*Director of the United States Patent and Trademark Office*